(12) United States Patent
Bandman et al.

(10) Patent No.: US 6,264,947 B1
(45) Date of Patent: Jul. 24, 2001

(54) PROTEIN KINASE HOMOLOGS

(75) Inventors: Olga Bandman, Mountain View; Y. Tom Tang, San Jose; Jennifer L. Hillman, Mountain View; Henry Yue, Sunnyvale; Karl J. Guegler, Menlo Park; Neil C. Corley, Mountain View; Gina A. Gorgone, Boulder Creek; Yalda Azimzai, Union City; Dyung Aina M. Lu, San Jose, all of CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 09/420,915

(22) Filed: Oct. 20, 1999

Related U.S. Application Data

(62) Division of application No. 09/173,581, filed on Oct. 15, 1998, now Pat. No. 6,013,455.

(51) Int. Cl.⁷ .............................. A61K 38/51; C12N 9/12; C07K 1/00
(52) U.S. Cl. ........................... 424/94.5; 435/194; 530/350
(58) Field of Search ......................... 424/94.5; 435/194; 530/350

(56) References Cited

U.S. PATENT DOCUMENTS 5,968,800 * 11/1999 Gerhold et al. ...................... 435/194

OTHER PUBLICATIONS

Koegl et al., Biochem. J., 303, 749–753, Jul. 1994.*
Eck et al., Nature, 68, 764–769, Apr. 1994.*
Kim et al., J.B.C., 273(40), 25875–25879, Nov. 1998.*
Letwin et al., EMBO J., 11(10), 3521–3531, Jul. 1992.*
Hardie, G. and Hanks, S., *The Protein Kinase Facts Book*, vol. I: 7–20 Academic Press, San Diego, CA (1995).
Charbonneau, H. and Tonks, N.K., "1002 PROTEIN PHOSPHATASES?", *Annu. Rev. Cell Biol.* 8: 463–493 (1992).

* cited by examiner

*Primary Examiner*—Rebecca E. Prouty
*Assistant Examiner*—Maryam Monshipouri
(74) *Attorney, Agent, or Firm*—Incyte Genomics, Inc.

(57) ABSTRACT

The invention provides human protein kinase homologs (PKH) and polynucleotides which identify and encode PKH. The invention also provides expression vectors, host cells, antibodies, agonists, and antagonists. The invention also provides methods for diagnosing, treating or preventing disorders associated with expression of PKH.

4 Claims, No Drawings

PROTEIN KINASE HOMOLOGS

This application is a divisional application of U.S. application Ser. No. 09/173,581, filed Oct. 15, 1998 now U.S. Pat. No. 6,013,455 issued Jan. 11, 2000.

FIELD OF THE INVENTION

This invention relates to nucleic acid and amino acid sequences of protein kinase homologs and to the use of these sequences in the diagnosis, treatment, and prevention of cancer, autoimmune/inflammatory disorders, and reproductive disorders.

BACKGROUND OF THE INVENTION

Kinases and phosphatases are critical components of intracellular signal transduction mechanisms. Kinases catalyze the transfer of high energy phosphate groups from adenosine triphosphate (ATP) to hydroxyamino acids of various target proteins. Phosphatases, in contrast, remove phosphate groups from proteins. Reversible protein phosphorylation is the main strategy for regulating protein activity in eukaryotic cells. In general, proteins are activated by phosphorylation in response to extracellular signals such as hormones, neurotransmitters, and growth and differentiation factors. Protein dephosphorylation occurs when downregulation of a signaling pathway is required. The combined activities of kinases and phosphatases regulate key cellular processes such as proliferation, differentiation, and cell cycle progression.

Kinases comprise the largest known enzyme superfamily and vary widely in their target proteins. Kinases may be categorized as protein tyrosine kinases (PTKs), which phosphorylate tyrosine residues, and protein serine/threonine kinases (STKs), which phosphorylate serine and/or threonine residues. Some kinases have dual specificity for both serine/threonine and tyrosine residues. Almost all kinases contain a conserved 250–300 amino acid catalytic domain. This domain can be further divided into 11 subdomains. N-terminal subdomains I–IV fold into a two-lobed structure which binds and orients the ATP donor molecule, and subdomain V spans the two lobes. C-terminal subdomains VI–XI bind the protein substrate and transfer the gamma phosphate from ATP to the hydroxyl group of a serine, threonine, or tyrosine residue. Each of the 11 subdomains contains specific catalytic residues or amino acid motifs characteristic of that subdomain. For example, subdomain I contains an 8-amino acid glycine-rich ATP binding consensus motif, subdomain II contains a critical lysine residue required for maximal catalytic activity, and subdomains VI through IX comprise the highly conserved catalytic core. STKs and PTKs also contain distinct sequence motifs in subdomains VI and VIII which may confer hydroxyamino acid specificity. Some STKs and PTKs possess structural characteristics of both families. In addition, kinases may also be classified by additional amino acid sequences, generally between 5 and 100 residues, which either flank or occur within the kinase domain. These additional amino acid sequences regulate kinase activity and determine substrate specificity. (Reviewed in Hardie, G. and Hanks, S. (1995) *The Protein Kinase Facts Book*, Vol I:7–20 Academic Press, San Diego, Calif.)

PTKs may be classified as either transmembrane or non-transmembrane proteins. Transmembrane tyrosine kinases function as receptors for most growth factors. Binding of growth factor to the receptor activates the transfer of a phosphate group from ATP to selected tyrosine residues in the receptor itself and in specific second messenger proteins. Growth factors (GF) that associate with receptor PTKs include epidermal GF, platelet-derived GF, fibroblast GF, hepatocyte GF, insulin and insulin-like GFs, nerve GF, vascular endothelial GF, and macrophage colony stimulating factor.

Non-transmembrane PTKs form signaling complexes with the cytosolic domains of plasma membrane receptors. Receptors that signal through non-transmembrane PTKs include cytokine, hormone, and antigen-specific lymphocytic receptors. Many PTKs were first identified as oncogene products in cancer cells in which PTK activation was no longer subject to normal cellular controls. In fact, about one third of the known oncogenes encode PTKs. Furthermore, cellular transformation (oncogenesis) is often accompanied by increased tyrosine phosphorylation activity. (Carbonneau, H. and Tonks, N. K. (1992) Annu. Rev. Cell Biol. 8:463–93.) Regulation of PTK activity may therefore be an important strategy in controlling some types of cancer.

The discovery of new protein kinase homologs and the polynucleotides encoding them satisfies a need in the art by providing new compositions which are useful in the diagnosis, prevention, and treatment of cancer, autoimmune/inflammatory disorders, and reproductive disorders.

SUMMARY OF THE INVENTION

The invention features substantially purified polypeptides, protein kinase homologs, referred to collectively as "PKH" and individually as "PKH-1", "PKH-2", "PKH-3", "PKH-4", "PKH-5", "PKH-6", "PKH-7", "PKH-8", and "PKH-9". In one aspect, the invention provides a substantially purified polypeptide comprising an amino acid sequence selected from the group consisting of SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, (SEQ ID NO: 1–9), and fragments thereof.

The invention further provides a substantially purified variant having at least 90% amino acid identity to at least one of the amino acid sequences selected from the group consisting of SEQ ID NO: 1–9, and fragments thereof. The invention also provides an isolated and purified polynucleotide encoding the polypeptide comprising an amino acid sequence selected from the group consisting of SEQ ID NO: 1–9, and fragments thereof. The invention also includes an isolated and purified polynucleotide variant having at least 70% polynucleotide sequence identity to the polynucleotide encoding the polypeptide comprising an amino acid sequence selected from the group consisting of SEQ ID NO: 1–9, and fragments thereof.

Additionally, the invention provides an isolated and purified polynucleotide which hybridizes under stringent conditions to the polynucleotide encoding the polypeptide comprising an amino acid sequence selected from the group consisting of SEQ ID NO: 1–9, and fragments thereof. The invention also provides an isolated and purified polynucleotide having a sequence which is complementary to the polynucleotide encoding the polypeptide comprising the amino acid sequence selected from the group consisting of SEQ ID NO: 1–9, and fragments thereof.

The invention also provides an isolated and purified polynucleotide comprising a polynucleotide sequence selected from the group consisting of SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, (SEQ ID NO: 10–18) and fragments thereof. The invention further provides an isolated and purified polynucleotide variant having at least 70% polynucleotide sequence identity to the polynucleotide sequence selected from the group consisting of SEQ ID NO: 10–18, and fragments thereof. The invention also provides an isolated and purified polynucleotide having a sequence which is complementary to the polynucleotide comprising a polynucleotide sequence selected from the group consisting of SEQ ID NO: 10–18, and fragments thereof.

The invention also provides a method for detecting a polynucleotide in a sample containing nucleic acids, the method comprising the steps of (a) hybridizing the complement of the polynucleotide sequence to at least one of the polynucleotides of the sample, thereby forming a hybridization complex; and (b) detecting the hybridization complex, wherein the presence of the hybridization complex correlates with the presence of a polynucleotide in the sample. In one aspect, the method further comprises amplifying the polynucleotide prior to hybridization.

The invention further provides an expression vector containing at least a fragment of the polynucleotide encoding the polypeptide comprising an amino acid sequence selected from the group consisting of SEQ ID NO: 1–9, and fragments thereof. In another aspect, the expression vector is contained within a host cell.

The invention also provides a method for producing a polypeptide, the method comprising the steps of: (a) culturing the host cell containing an expression vector containing at least a fragment of a polynucleotide under conditions suitable for the expression of the polypeptide; and (b) recovering the polypeptide from the host cell culture.

The invention also provides a pharmaceutical composition comprising a substantially purified polypeptide having the amino acid sequence selected from the group consisting of SEQ ID NO: 1–9, and fragments thereof, in conjunction with a suitable pharmaceutical carrier.

The invention further includes a purified antibody which binds to a polypeptide selected from the group consisting of SEQ ID NO: 1–9, and fragments thereof. The invention also provides a purified agonist and a purified antagonist to the polypeptide.

The invention also provides a method for treating or preventing a disorder of cell proliferation associated with decreased expression or activity of PKH, the method comprising administering to a subject in need of such treatment an effective amount of a pharmaceutical composition comprising a substantially purified polypeptide having the amino acid sequence selected from the group consisting of SEQ ID NO: 1–9, and fragments thereof, in conjunction with a suitable pharmaceutical carrier.

The invention also provides a method for treating or preventing a disorder of cell proliferation associated with increased expression or activity of PKH, the method comprising administering to a subject in need of such treatment an effective amount of an antagonist of a polypeptide having an amino acid sequence selected from the group consisting of SEQ ID NO: 1–9, and fragments thereof.

BRIEF DESCRIPTION OF THE TABLES

Table 1 shows nucleotide and polypeptide sequence identification numbers (SEQ ID NO), clone identification numbers (clone ID), cDNA libraries, and cDNA fragments used to assemble full-length sequences encoding PKH.

Table 2 shows features of each polypeptide sequence including potential motifs, homologous sequences, and methods and algorithms used for characterization of PKH.

Table 3 shows the tissue-specific expression patterns of each nucleic acid sequence as determined by northern analysis, diseases, disorders, or conditions associated with these tissues, and the vector into which each cDNA was cloned.

Table 4 describes the tissues used to construct the cDNA libraries from which Incyte cDNA clones encoding PKH were isolated.

Table 5 shows the programs, their descriptions, references, and threshold parameters used to analyze PKH.

DESCRIPTION OF THE INVENTION

Before the present proteins, nucleotide sequences, and methods are described, it is understood that this invention is not limited to the particular machines, materials and methods described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any machines, materials, and methods similar or equivalent to those described herein can be used to practice or test the present invention, the preferred machines, materials and methods are now described. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

DEFINITIONS

"PKH" refers to the amino acid sequences of substantially purified PKH obtained from any species, particularly a mammalian species, including bovine, ovine, porcine, murine, equine, and preferably the human species, from any source, whether natural, synthetic, semi-synthetic, or recombinant.

The term "agonist" refers to a molecule which, when bound to PKH, increases or prolongs the duration of the effect of PKH. Agonists may include proteins, nucleic acids, carbohydrates, or any other molecules which bind to and modulate the effect of PKH.

An "allelic variant" is an alternative form of the gene encoding PKH. Allelic variants may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to allelic variants are generally ascribed to natural deletions, additions, or substitutions of nucleotides. Each of these types of changes may occur alone, or in combination with the others, one or more times in a given sequence.

"Altered" nucleic acid sequences encoding PKH include those sequences with deletions, insertions, or substitutions of different nucleotides, resulting in a polynucleotide the same as PKH or a polypeptide with at least one functional characteristic of PKH. Included within this definition are polymorphisms which may or may not be readily detectable using a particular oligonucleotide probe of the polynucleotide encoding PKH, and improper or unexpected hybridization to allelic variants, with a locus other than the normal chromosomal locus for the polynucleotide sequence encoding PKH. The encoded protein may also be "altered," and may contain deletions, insertions, or substitutions of amino acid residues which produce a silent change and result in a functionally equivalent PKH. Deliberate amino acid substitutions may be made on the basis of similarity in polarity, charge, solubility, hydrophobicity, hydrophilicity, and/or the amphipathic nature of the residues, as long as the biological or immunological activity of PKH is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence" refer to an oligopeptide, peptide, polypeptide, or protein sequence, or a fragment of any of these, and to naturally occurring or synthetic molecules. In this context, "fragments," "immunogenic fragments," or "antigenic fragments" refer to fragments of PKH which are preferably at least 5 to about 15 amino acids in length, most preferably at least 14 amino acids, and which retain some biological activity or immunological activity of PKH. Where "amino acid sequence" is recited to refer to an amino acid sequence of a naturally occurring protein molecule, "amino acid sequence" and like terms are not meant to limit the amino acid sequence to the complete native amino acid sequence associated with the recited protein molecule.

"Amplification" relates to the production of additional copies of a nucleic acid sequence. Amplification is generally carried out using polymerase chain reaction (PCR) technologies well known in the art.

The term "antagonist" refers to a molecule which, when bound to PKH, decreases the amount or the duration of the effect of the biological or immunological activity of PKH. Antagonists may include proteins, nucleic acids, carbohydrates, antibodies, or any other molecules which decrease the effect of PKH.

The term "antibody" refers to intact molecules as well as to fragments thereof, such as Fab, $F(ab')_2$, and Fv fragments, which are capable of binding the epitopic determinant. Antibodies that bind PKH polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant" refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense" refers to any composition containing a nucleic acid sequence which is complementary to the "sense" strand of a specific nucleic acid sequence. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

The term "biologically active," refers to a protein having structural, regulatory, or biochemical functions of a naturally occurring molecule. Likewise, "immunologically active" refers to the capability of the natural, recombinant, or synthetic PKH, or of any oligopeptide thereof, to induce a specific immune response in appropriate animals or cells and to bind with specific antibodies.

The terms "complementary" or "complementarity" refer to the natural binding of polynucleotides by base pairing. For example, the sequence "5' A-G-T 3'" bonds to the complementary sequence "3' T-C-A 5'." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence" refer broadly to any composition containing the given polynucleotide or amino acid sequence. The composition may comprise a dry formulation or an aqueous solution. Compositions comprising polynucleotide sequences encoding PKH or fragments of PKH may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., sodium dodecyl sulfate; SDS), and other components (e.g., Denhardt's solution, dry milk, salmon sperm DNA, etc.).

"Consensus sequence" refers to a nucleic acid sequence which has been resequenced to resolve uncalled bases, extended using XL-PCR kit (Perkin-Elmer, Norwalk Conn.) in the 5' and/or the 3' direction, and resequenced, or which has been assembled from the overlapping sequences of more than one Incyte Clone using a computer program for fragment assembly, such as the GELVIEW fragment assembly system (GCG, Madison Wis.). Some sequences have been both extended and assembled to produce the consensus sequence.

The term "correlates with expression of a polynucleotide" indicates that the detection of the presence of nucleic acids, the same or related to a nucleic acid sequence encoding PKH, by northern analysis is indicative of the presence of nucleic acids encoding PKH in a sample, and thereby correlates with expression of the transcript from the polynucleotide encoding PKH.

A "deletion" refers to a change in the amino acid or nucleotide sequence that results in the absence of one or more amino acid residues or nucleotides.

The term "derivative" refers to the chemical modification of a polypeptide sequence, or a polynucleotide sequence. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "similarity" refers to a degree of complementarity. There may be partial similarity or complete similarity. The word "identity" may substitute for the word "similarity." A partially complementary sequence that at least partially inhibits an identical sequence from hybridizing to a target nucleic acid is referred to as "substantially similar." The inhibition of hybridization of the completely complementary sequence to the target sequence may be examined using a hybridization assay (Southern or northern blot, solution hybridization, and the like) under conditions of reduced stringency. A substantially similar sequence or hybridization probe will compete for and inhibit the binding of a completely similar (identical) sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% similarity or identity). In the absence of non-specific binding, the substantially similar sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MEGALIGN program (DNASTAR, Madison Wis.) which creates alignments between two or more sequences according to methods selected by the user, e.g., the clustal method. (See, e.g., Higgins, D. G. and P. M. Sharp (1988) Gene 73:237–244.) The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between nucleic acid sequences can also be counted or calculated by other methods known in the art, e.g., the Jotun Hein method. (See, e.g., Hein, J. (1990) Methods Enzymol. 183:626–645.) Identity between sequences can also be determined by other methods known in the art, e.g., by varying hybridization conditions.

"Human artificial chromosomes" (HACs) are linear microchromosomes which may contain DNA sequences of about 6 kb to 10 Mb in size, and which contain all of the elements required for stable mitotic chromosome segregation and maintenance.

The term "humanized antibody" refers to antibody molecules in which the amino acid sequence in the non-antigen binding regions has been altered so that the antibody more closely resembles a human antibody, and still retains its original binding ability.

"Hybridization" refers to any process by which a strand of nucleic acid binds with a complementary strand through base pairing.

The term "hybridization complex" refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition" refer to changes in an amino acid or nucleotide sequence resulting in the addition of one or more amino acid residues or nucleotides, respectively, to the sequence found in the naturally occurring molecule.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The term "microarray" refers to an arrangement of distinct polynucleotides on a substrate.

The terms "element" or "array element" in a microarray context, refer to hybridizable polynucleotides arranged on the surface of a substrate.

The term "modulate" refers to a change in the activity of PKH. For example, modulation may cause an increase or a decrease in protein activity, binding characteristics, or any other biological, functional, or immunological properties of PKH.

The phrases "nucleic acid" or "nucleic acid sequence" refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which, when translated, would produce polypeptides retaining some functional characteristic, e.g., antigenicity, or structural domain characteristic, e.g., ATP-binding site, of the full-length polypeptide.

The terms "operably associated" or "operably linked" refer to functionally related nucleic acid sequences. A promoter is operably associated or operably linked with a coding sequence if the promoter controls the translation of the encoded polypeptide. While operably associated or operably linked nucleic acid sequences can be contiguous and in the same reading frame, certain genetic elements, e.g., repressor genes, are not contiguously linked to the sequence encoding the polypeptide but still bind to operator sequences that control expression of the polypeptide.

The term "oligonucleotide" refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. "Oligonucleotide" is substantially equivalent to the terms "amplimer," "primer," "oligomer," and "probe," as these terms are commonly defined in the art.

"Peptide nucleic acid" (PNA) refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell.

The term "sample" is used in its broadest sense. A sample suspected of containing nucleic acids encoding PKH, or fragments thereof, or PKH itself, may comprise a bodily fluid; an extract from a cell, chromosome, organelle, or membrane isolated from a cell; a cell; genomic DNA, RNA, or cDNA, in solution or bound to a substrate; a tissue; a tissue print; etc.

The terms "specific binding" or "specifically binding" refer to that interaction between a protein or peptide and an agonist, an antibody, or an antagonist. The interaction is dependent upon the presence of a particular structure of the protein, e.g., the antigenic determinant or epitope, recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

The term "stringent conditions" refers to conditions which permit hybridization between polynucleotides and the claimed polynucleotides. Stringent conditions can be defined by salt concentration, the concentration of organic solvent, e.g., formamide, temperature, and other conditions well known in the art. In particular, stringency can be increased by reducing the concentration of salt, increasing the concentration of formamide, or raising the hybridization temperature.

The term "substantially purified" refers to nucleic acid or amino acid sequences that are removed from their natural environment and are isolated or separated, and are at least about 60% free, preferably about 75% free, and most preferably about 90% free from other components with which they are naturally associated.

A "substitution" refers to the replacement of one or more amino acids or nucleotides by different amino acids or nucleotides, respectively.

"Substrate" refers to any suitable rigid or semi-rigid support including membranes, filters, chips, slides, wafers, fibers, magnetic or nonmagnetic beads, gels, tubing, plates, polymers, microparticles and capillaries. The substrate can have a variety of surface forms, such as wells, trenches, pins, channels and pores, to which polynucleotides or polypeptides are bound.

"Transformation" describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, as well as transiently transformed cells which express the inserted DNA or RNA for limited periods of time.

A "variant" of PKH polypeptides refers to an amino acid sequence that is altered by one or more amino acid residues. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE software (DNASTAR).

The term "variant," when used in the context of a polynucleotide sequence, may encompass a polynucleotide sequence related to PKH. This definition may also include, for example, "allelic" (as defined above), "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPS) in which the polynucleotide sequence varies by one base. The presence of SNPs may be indicative of, for example, a certain population, a disease state, or a propensity for a disease state.

THE INVENTION

The invention is based on the discovery of new human protein kinase homologs (PKH), the polynucleotides encoding PKH, and the use of these compositions for the diagnosis, treatment, or prevention of cancer, autoimmune/inflammatory disorders, and reproductive disorders.

Table 1 lists the Incyte Clones used to derive full length nucleotide sequences encoding PKH. Columns 1 and 2 show the sequence identification numbers (SEQ ID NO) of the amino acid and nucleic acid sequences, respectively. Column 3 shows the Clone ID of the Incyte Clone in which nucleic acids encoding each PKH were identified, and column 4, the cDNA libraries from which these clones were isolated. Column 5 shows Incyte clones, their corresponding cDNA libraries, and shotgun sequences. The clones and shotgun sequences are part of the consensus nucleotide sequence of each PKH and are useful as fragments in hybridization technologies.

The columns of Table 2 show various properties of the polypeptides of the invention: column 1 references the amino acid SEQ ID NO; column 2 shows the number of amino acid residues in each polypeptide; column 3, potential phosphorylation sites; column 4, the amino acid residues comprising signature sequences and motifs; column 5, the identity of each protein; and column 6, analytical methods used to characterize and identify each protein through sequence homology and protein motifs.

The columns of Table 3 show the tissue specificity and diseases, disorders, or conditions associated with nucleotide sequences encoding PKH. The first column of Table 3 lists the nucleotide SEQ ID NO; the second column lists tissue categories which express PKH as a fraction of total tissue categories expressing PKH. The third column lists the diseases, disorders, or conditions associated with those tissues expressing PKH. The fourth column lists the vectors used to subclone the cDNA library.

The following fragments of the nucleotide sequences encoding PKH are useful in hybridization or amplification technologies to identify SEQ ID NO: 10–18 and to distinguish between SEQ ID NO: 10–18 and related polynucleotide sequences. The useful fragments are the fragment of SEQ ID NO: 10 from about nucleotide 473 to about nucleotide 532; the fragment of SEQ ID NO: 11 from about nucleotide 65 to about nucleotide 125; the fragment of SEQ ID NO:12 from about nucleotide 96 to about nucleotide 155; the fragment of SEQ ID NO:13 from about nucleotide 805 to about nucleotide 864; the fragment of SEQ ID NO: 14 from about nucleotide 230 to about nucleotide 289; the fragment of SEQ ID NO: 15 from about nucleotide 154 to about nucleotide 213; the fragment of SEQ ID NO:16 from about nucleotide 110 to about nucleotide 169; the fragment of SEQ ID NO: 17 from about nucleotide 482 to about nucleotide 541; and the fragment of SEQ ID NO: 18 from about nucleotide 115 to about nucleotide 174.

The invention also encompasses PKH variants. A preferred PKH variant is one which has at least about 80%, more preferably at least about 90%, and most preferably at least about 95% amino acid sequence identity to the PKH amino acid sequence, and which contains at least one functional or structural characteristic of PKH.

The invention also encompasses polynucleotides which encode PKH. In a particular embodiment, the invention encompasses a polynucleotide sequence comprising a sequence selected from the group consisting of SEQ ID NO: 10–18, which encodes PKH.

The invention also encompasses a variant of a polynucleotide sequence encoding PKH. In particular, such a variant polynucleotide sequence will have at least about 70%, more preferably at least about 85%, and most preferably at least about 95% polynucleotide sequence identity to the polynucleotide sequence encoding PKH. A particular aspect of the invention encompasses a variant of a polynucleotide sequence comprising a sequence selected from the group consisting of SEQ ID NO: 10–18 which has at least about 70%, more preferably at least about 85%, and most preferably at least about 95% polynucleotide sequence identity to a nucleic acid sequence selected from the group consisting of SEQ ID NO: 10–18. Any one of the polynucleotide variants described above can encode an amino acid sequence which contains at least one functional or structural characteristic of PKH.

It will be appreciated by those skilled in the art that as a result of the degeneracy of the genetic code, a multitude of polynucleotide sequences encoding PKH, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring PKH, and all such variations are to be considered as being specifically disclosed.

Although nucleotide sequences which encode PKH and its variants are preferably capable of hybridizing to the nucleotide sequence of the naturally occurring PKH under appropriately selected conditions of stringency, it may be advantageous to produce nucleotide sequences encoding PKH or its derivatives possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding PKH and its derivatives without altering the encoded amino acid sequences include the production of RNA transcripts having more desirable properties, such as a greater half-life, than transcripts produced from the naturally occurring sequence.

The invention also encompasses production of DNA sequences which encode PKH and PKH derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding PKH or any fragment thereof.

Also encompassed by the invention are polynucleotide sequences that are capable of hybridizing to the claimed polynucleotide sequences, and, in particular, to those shown in SEQ ID NO: 10–18 and fragments thereof under various conditions of stringency. (See, e.g., Wahl, G. M. and S. L. Berger (1987) Methods Enzymol. 152:399–407; Kimmel, A. R. (1987) Methods Enzymol. 152:507–511.) For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μ/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

The washing steps which follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include temperature of at least about 25° C., more preferably of at least about 42° C., and most preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a most preferred embodiment, wash steps will occur at 68° C. in 15 mM NaCl, 1.5 mM trisodium citrate, and 0.1% SDS. Additional variations on these conditions will be readily apparent to those skilled in the art.

Methods for DNA sequencing are well known in the art and may be used to practice any of the embodiments of the invention. The methods may employ such enzymes as the Klenow fragment of DNA polymerase I, SEQUENASE (US Biochemical, Cleveland Ohio), Taq polymerase (Perkin-Elmer), thermostable T7 polymerase (Amersham Pharmacia Biotech, Piscataway N.J.), or combinations of polymerases and proofreading exonucleases such as those found in the ELONGASE amplification system (Life Technologies, Gaithersburg Md.). Preferably, sequence preparation is automated with machines such as the MICROLAB 2200 (Hamilton, Reno Nev.), Peltier thermal cycler 200 (PTC200; MJ Research, Watertown Mass.) and the ABI CATALYST 800 (Perkin-Elmer). Sequencing is then carried out using either ABI 373 or 377 DNA sequencing systems (Perkin-Elmer) or the MEGABACE 1000 DNA sequencing system (Molecular Dynamics, Sunnyvale Calif.). The resulting sequences are analyzed using a variety of algorithms which are well known in the art. (See, e.g., Ausubel, F. M. (1997) *Short Protocols in Molecular Biology*, John Wiley & Sons, New York N.Y., unit 7.7; Meyers, R. A. (1995) *Molecular Biolog and Biotechnology*, Wiley VCH, New York N.Y., pp. 856–853.)

The nucleic acid sequences encoding PKH may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector. (See, e.g., Sarkar, G. (1993) PCR Methods Applic. 2:318–322.) Another method, inverse PCR, uses primers that extend in divergent directions to amplify unknown sequence from a circularized template. The template is derived from restriction fragments comprising a known genomic locus and surrounding sequences. (See, e.g., Triglia, T. et al. (1988) Nucleic Acids Res. 16:8186.) A third method, capture PCR, involves PCR amplification of DNA fragments adjacent to known sequences in human and yeast artificial chromosome DNA. (See, e.g., Lagerstrom, M. et al. (1991) PCR Methods Applic. 1:111–119.) In this method, multiple restriction enzyme digestions and ligations may be used to insert an engineered double-stranded sequence into a region of unknown sequence before performing PCR. Other methods which may be used to retrieve unknown sequences are known in the art. (See, e.g., Parker, J. D. et al. (1991) Nucleic Acids Res. 19:3055–306). Additionally, one may use PCR, nested primers, and PROMOTERFINDER libraries (Clontech, Palo Alto Calif.) to walk genomic DNA. This procedure avoids the need to screen libraries and is useful in finding intron/exon junctions. For all PCR-based methods, primers may be designed using commercially available software, such as OLIGO 4.06 Primer analysis software (National Biosciences, Plymouth Minn.) or another appropriate program, to be about 22 to 30 nucleotides in length, to have a GC content of about 50% or more, and to anneal to the template at temperatures of about 68° C. to 72° C.

When screening for full-length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., GENOTYPER and SEQUENCE NAVIGATOR, Perkin-Elmer), and the entire process from loading of samples to computer analysis and electronic data display may be computer controlled. Capillary electrophoresis is especially preferable for sequencing small DNA fragments which may be present in limited amounts in a particular sample.

In another embodiment of the invention, polynucleotide sequences or fragments thereof which encode PKH may be cloned in recombinant DNA molecules that direct expression of PKH, or fragments or functional equivalents thereof, in appropriate host cells. Due to the inherent degeneracy of the genetic code, other DNA sequences which encode substantially the same or a functionally equivalent amino acid sequence may be produced and used to express PKH.

The nucleotide sequences of the present invention can be engineered using methods generally known in the art in order to alter PKH-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In another embodiment, sequences encoding PKH may be synthesized, in whole or in part, using chemical methods well known in the art. (See, e.g., Caruthers, M. H. et al. (1980) Nucl. Acids Res. Symp. Ser. 215–223, and Horn, T. et al. (1980) Nucl. Acids Res. Symp. Ser. 225–232.) Alternatively, PKH itself or a fragment thereof may be synthesized using chemical methods. For example, peptide synthesis can be performed using various solid-phase techniques. (See, e.g., Roberge, J. Y. et al. (1995) Science 269:202–204.) Automated synthesis may be achieved using the ABI 431A Peptide synthesizer (Perkin-Elmer). Additionally, the amino acid sequence of PKH, or any part thereof, may be altered during direct synthesis and/or combined with sequences from other proteins, or any part thereof, to produce a variant polypeptide.

The peptide may be substantially purified by preparative high performance liquid chromatography. (See, e.g, Chiez, R. M. and F. Z. Regnier (1990) Methods Enzymol.

182:392–421.) The composition of the synthetic peptides may be confirmed by amino acid analysis or by sequencing. (See, e.g., Creighton, T. (1984) *Proteins, Structures and Molecular Properties*, WH Freeman, New York N.Y.)

In order to express a biologically active PKH, the nucleotide sequences encoding PKH or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotide sequences encoding PKH. Such elements may vary in their strength and specificity. Specific initiation signals may also be used to achieve more efficient translation of sequences encoding PKH. Such signals include the ATG initiation codon and adjacent sequences, e.g. the Kozak sequence. In cases where sequences encoding PKH and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used. (See, e.g., Scharf, D. et al. (1994) Results Probl. Cell Differ. 20:125–162.)

Methods which are well known to those skilled in the art may be used to construct expression vectors containing sequences encoding PKH and appropriate transcriptional and translational control elements. These methods include in vitro recombinant DNA techniques, synthetic techniques, and in vivo genetic recombination. (See, e.g., Sambrook, J. et al. (1989) *Molecular Cloning, A Laboratory Manual*, old Spring Harbor Press, Plainview N.Y., ch. 4, 8, and 16–17; Ausubel, F. M. et al. (1995) *Current Protocols in Molecular Biology*, John Wiley & Sons, New York N.Y., ch. 9, 13, and 16.)

A variety of expression vector/host systems may be utilized to contain and express sequences encoding PKH. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus, CaMV, or tobacco mosaic virus, TMV) or with bacterial expression vectors (e.g., Ti or pBR322 plasmids); or animal cell systems. The invention is not limited by the host cell employed.

In bacterial systems, a number of cloning and expression vectors may be selected depending upon the use intended for polynucleotide sequences encoding PKH. For example, routine cloning, subcloning, and propagation of polynucleotide sequences encoding PKH can be achieved using a multifunctional *E. coli* vector such as PBLUESCRIPT (Stratagene, La Jolla Calif.) or PSPORT1 plasmid (Life Technologies). Ligation of sequences encoding PKH into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence. (See, e.g., Van Heeke, G. and S. M. Schuster (1989) J. Biol. Chem. 264:5503–5509.) When large quantities of PKH are needed, e.g. for the production of antibodies, vectors which direct high level expression of PKH may be used. For example, vectors containing the strong, inducible T5 or T7 bacteriophage promoter may be used.

Yeast expression systems may be used for production of PKH. A number of vectors containing constitutive or inducible promoters, such as alpha factor, alcohol oxidase, and PGH, may be used in the yeast *Saccharomyces cerevisiae* or *Pichia Rastoris*. In addition, such vectors direct either the secretion or intracellular retention of expressed proteins and enable integration of foreign sequences into the host genome for stable propagation. (See, e.g., Ausubel, 1995, supra; Grant et al. (1987) Methods Enzymol. 153:516–54; and Scorer, C. A. et al. (1994) Bio/Technology 12:181–184.)

Plant systems may also be used for expression of PKH. Transcription of sequences encoding PKH may be driven viral promoters, e.g., the 35S and 19S promoters of CaMV used alone or in combination with the omega leader sequence from TMV (Takamatsu, N. (1987) EMBO J. 6:307–311). Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. (See, e.g., *The McGraw Hill Yearbook of Science and Technology* (1992) McGraw Hill, New York N.Y., pp. 191–196.)

In mammalian cells, a number of viral-based expression systems may be utilized. In cases where an adenovirus is used as an expression vector, sequences encoding PKH may be ligated into an adenovirus transcription/translation complex consisting of the late promoter and tripartite leader sequence. Insertion in a non-essential E1 or E3 region of the viral genome may be used to obtain infective virus which expresses PKH in host cells. (See, e.g., Logan, J. and T. Shenk (1984) Proc. Natl. Acad. Sci. 8–1:3655–3659.) In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes. (See, e.g., Harrington, J. J. et al. (1997) Nat Genet. 15:345–355.)

For long term production of recombinant proteins in mammalian systems, stable expression of PKH in cell lines is preferred. For example, sequences encoding PKH can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in tk⁻ or apr⁻ cells, respectively. (See, e.g., Wigler, M. et al. (1977) Cell 11:223–232; Lowy, I. et al. (1980) Cell 22:817–823.) Also, antimetabolite, antibiotic, or herbicide resistance can be used as the basis for selection. For example, dhfr confers resistance to methotrexate; neo confers resistance to the. aminoglycosides, neomycin and G-418; and als and pat confer resistance to chlorsulfuron and phosphinotricin acetyltransferase, respectively. (See, e.g., Wigler, M. et al. (1980) Proc. Natl. Acad. Sci. 77:3567–3570; Colbere-Garapin, F. et al. (1981) J. Mol. Biol. 150:1–14.) Additional selectable genes have been described, e.g., trpB and hisD, which alter cellular requirements for metabolites. (See, e.g., Hartman, S. C. and R. C. Mulligan (1988) Proc. Natl. Acad. Sci. 85:8047–8051.) Visible markers, e.g., anthocyanins, green fluorescent proteins (GFP; Clontech), β glucuronidase and its substrate β-glucuronide, or luciferase and its substrate luciferin may be used. These markers can be used not only to identify transformants, but also to quantify the amount of transient or stable protein expression attributable to a specific vector system. (See, e.g., Rhodes, C. A. (1995) Methods Mol. Biol. 55:121–131.)

Although the presence/absence of marker gene expression suggests that the gene of interest is also present, the presence and expression of the gene may need to be confirmed. For example, if the sequence encoding PKH is inserted within a marker gene sequence, transformed cells containing sequences encoding PKH can be identified by the absence of marker gene function. Alternatively, a marker gene can be placed in tandem with a sequence encoding PKH under the control of a single promoter. Expression of the marker gene in response to induction or selection usually indicates expression of the tandem gene as well.

In general, host cells that contain the nucleic acid sequence encoding PKH and that express PKH may be identified by a variety of procedures known to those of skill in the art. These procedures include, but are not limited to, DNA-DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of PKH using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on PKH is preferred, but a competitive binding assay may be employed. These and other assays are well known in the art. (See, e.g., Hampton, R. et al. (1990) *Serological Methods, a Laboratory Manual*, APS Press, St Paul Minn., Sect. IV; Coligan, J. E. et al. (1997) *Current Protocols in Immunology*, Greene Pub. Associates and Wiley-Interscience, New York N.Y.; and Pound, J. D. (1998) Immunochemical Protocols, Humana Press, Totowa N.J.).

A wide variety of labels and conjugation techniques are known by those skilled in the art and may be used in various nucleic acid and amino acid assays. Means for producing labeled hybridization or PCR probes for detecting sequences related to polynucleotides encoding PKH include oligolabeling, nick translation, end-labeling, or PCR amplification using a labeled nucleotide. Alternatively, the sequences encoding PKH, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Amersham Pharmacia Biotech, Promega (Madison Wis.), and US Biochemical. Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding PKH may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode PKH may be designed to contain signal sequences which direct secretion of PKH through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to specify protein targeting, folding, and/or activity. Different host cells which have specific cellular machinery and characteristic mechanisms for post-translational activities (e.g., CHO, HeLa, MDCK, HEK293, and WI38), are available from the American Type Culture Collection (ATCC, Manassas Va.) and may be chosen to ensure the correct modification and processing of the foreign protein.

In another embodiment of the invention, natural, modified, or recombinant nucleic acid sequences encoding PKH may be ligated to a heterologous sequence resulting in translation of a fusion protein in any of the aforementioned host systems. For example, a chimeric PKH protein containing a heterologous moiety that can be recognized by a commercially available antibody may facilitate the screening of peptide libraries for inhibitors of PKH activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His enable purification of their cognate fusion proteins on immobilized glutathione, maltose, phenylarsine oxide, calmodulin, and metal-chelate resins, respectively. FLAG, c-myc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the PKH encoding sequence and the heterologous protein sequence, so that PKH may be cleaved away from the heterologous moiety following purification. Methods for fusion protein expression and purification are discussed in Ausubel (1995, supra, ch 10). A variety of commercially available kits may also be used to facilitate expression and purification of fusion proteins.

In a further embodiment of the invention, synthesis of radiolabeled PKH may be achieved in vitro using the TNT rabbit reticulocyte lysate or wheat germn extract systems (Promega). These systems couple transcription and translation of protein-coding sequences operably associated with the T7, T3, or SP6 promoters. Translation takes place in the presence of a radiolabeled amino acid precursor, preferably $^{35}S$-methionine.

Fragments of PKH may be produced not only by recombinant production, but also by direct peptide synthesis using solid-phase techniques. (See, e.g., Creighton, supra, pp. 55–60.) Protein synthesis may be performed by manual techniques or by automation. Automated synthesis may be achieved, for example, using the ABI 431A Peptide synthesizer (Perkin-Elmer). Various fragments of PKH may be synthesized separately and then combined to produce the full length molecule.

THERAPEUTICS

Chemical and structural similarity, e.g., in the context of sequences and motifs, exists between regions of PKE and various protein kinase homologs. In addition, the expression of PKH is closely associated with cancer, reproductive tissues and hematopoietic/immune tissues. Therefore, PKH appears to play a role in cancer, autoimmune/inflammatory disorders, and reproductive disorders. In the treatment of cancer, autoimmune/inflamratory disorders, and reproductive disorders associated with increased PKH expression or activity, it is desirable to decrease the expression or activity of PKH. In the treatment of the above conditions associated with decreased PKH expression or activity, it is desirable to increase the expression or activity of PKH.

Therefore, in one embodiment, PKH or a fragment or derivative thereof may be administered to a subject to treat or prevent a disorder associated with decreased expression or activity of PKH. Examples of such disorders include, but are not limited to, a cancer, such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; an autoimmune/inflammatory disorder such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, autoimmune polyenodocrinopathy-candidiasis-ectodermal dystrophy (APECED), bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma.; and a reproductive disorder, such as disorders of prolactin production; infertility, including tubal disease, ovulatory defects, and endometriosis; disruptions of the estrous cycle, disruptions of the menstrual cycle, polycystic ovary syndrome, ovarian hyperstimulation syndrome, endometrial and ovarian tumors, uterine fibroids, autoimmune disorders, ectopic pregnancies, and teratogenesis; cancer of the breast, fibrocystic breast disease, and galactorrhea; disruptions of spermatogenesis, abnormal sperm physiology, cancer of the testis, cancer of the prostate, benign prostatic hyperplasia, prostatitis, Peyronie's disease, impotence, carcinoma of the male breast, and gynecomastia.

In another embodiment, a vector capable of expressing PKH or a fragment or derivative thereof may be administered to a subject to treat or prevent a disorder associated with decreased expression or activity of PKH including, but not limited to, those described above.

In a further embodiment, a pharmaceutical composition comprising a substantially purified PKH in conjunction with a suitable pharmaceutical carrier may be administered to a subject to treat or prevent a disorder associated with decreased expression or activity of PKH including, but not limited to, those provided above.

In still another embodiment, an agonist which modulates the activity of PKH may be administered to a subject to treat or prevent a disorder associated with decreased expression or activity of PKH including, but not limited to, those listed above.

In a further embodiment, an antagonist of PKH may be administered to a subject to treat or prevent a disorder associated with increased expression or activity of PKH. Examples of such disorders include, but are not limited to, those described above. In one aspect, an antibody which specifically binds PKH may be used directly as an antagonist or indirectly as a targeting or delivery mechanism for bringing a pharmaceutical agent to cells or tissue which express PKH.

In an additional embodiment, a vector expressing the complement of the polynucleotide encoding PKH may be administered to a subject to treat or prevent a disorder associated with increased expression or activity of PKH including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of PKH may be produced using methods which are generally known in the art. In particular, purified PKH may be used to produce antibodies or to screen libraries of pharmaceutical agents to identify those which specifically bind PKH. Antibodies to PKH may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with PKH or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to PKH have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of PKH amino acids may be fused with those of another protein, such as KLH, and antibodies to the chimeric molecule may be produced.

Monoclonal antibodies to PKH may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce PKH-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:10134–10137.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86:3833–3837; Winter, G. et al. (1991) Nature 349:293–299.)

Antibody fragments which contain specific binding sites for PKH may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 246:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between PKH and its specific antibody. A two-site, monoclonal-based immunoassay utilizing monoclonal antibodies reactive to two non-interfering PKH epitopes is preferred, but a competitive binding assay may also be employed (Pound, supra).

Various methods such as Scatchard analysis in conjunction with radioimmunoassay techniques may be used to assess the affinity of antibodies for PKH. Affinity is expressed as an association constant, $K_a$, which is defined as the molar concentration of PKH-antibody complex divided by the molar concentrations of free antigen and free antibody under equilibrium conditions. The $K_a$ determined for a preparation of polyclonal antibodies, which are heterogeneous in their affinities for multiple PKH epitopes, represents the average affinity, or avidity, of the antibodies for PKH. The $K_a$ determined for a preparation of monoclonal antibodies, which are monospecific for a particular PKH epitope, represents a true measure of affinity. High-affinity antibody preparations with $K_a$ ranging from about $10^9$ to $10^{12}$ L/mole are preferred for use in immunoassays in which the PKH-antibody complex must withstand rigorous manipulations. Low-affinity antibody preparations with $K_a$ ranging from about $10^6$ to $10^7$ L/mole are preferred for use in immunopurification and similar procedures which ultimately require dissociation of PKH, preferably in active form, from the antibody (Catty, D. (1988) *Antibodies. Volume I: A Practical Approach*, IRL Press, Washington, D.C.; Liddell, J. E. and Cryer, A. (1991) *A Practical Guide to Monoclonal Antibodies*, John Wiley & Sons, New York N.Y.).

The titer and avidity of polyclonal antibody preparations may be further evaluated to determine the quality and suitability of such preparations for certain downstream applications. For example, a polyclonal antibody preparation containing at least 1–2 mg specific antibody/ml, preferably 5–10 mg specific antibody/ml, is preferred for use in procedures requiring precipitation of PKH-antibody complexes. Procedures for evaluating antibody specificity, titer, and avidity, and guidelines for antibody quality and usage in various applications, are generally available. (See, e.g., Catty, supra, and Coligan et al. supra.)

In another embodiment of the invention, the polynucleotides encoding PKH, or any fragment or complement thereof, may be used for therapeutic purposes. In one aspect, the complement of the polynucleotide encoding PKH may be used in situations in which it would be desirable to block the transcription of the mRNA. In particular, cells may be transformed with sequences complementary to polynucleotides encoding PKH. Thus, complementary molecules or fragments may be used to modulate PKH activity, or to achieve regulation of gene function. Such technology is now well known in the art, and sense or antisense oligonucleotides or larger fragments can be designed from various locations along the coding or control regions of sequences encoding PKH.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors to express nucleic acid sequences complementary to the polynucleotides encoding PKH. (See, e.g., Sambrook, supra; Ausubel, 1995, supra.)

Genes encoding PKH can be turned off by transforming a cell or tissue with expression vectors which express high levels-of a polynucleotide, or fragment thereof, encoding PKH. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding PKH. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing, Mt. Kisco N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of sequences encoding PKH.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding PKH. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1 997) Nature Biotechnology 15:462–466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of PKH, antibodies to PKH, and mimetics, agonists, antagonists, or inhibitors of PKH. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs, or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Reminigton's Pharmaceutical Sciences* (Maack Publishing, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acids. Salts tend to be imore soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5 5.5, that is combined with buffer prior to use.

After pharmaceutical compositions have been prepared, they can be placed in an appropriate container and labeled for treatment of an indicated condition. For administration of PKH, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example PKH or fragments thereof, antibodies of PKH, and agonists, antagonists or inhibitors of PKH, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of toxic to therapeutic effects is the therapeutic index, and it can be expressed as the $LD_{50}/ED_{50}$ ratio. Pharmaceutical compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

Normal dosage amounts may vary from about 0.1 µg to 100,000 µg, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind PKH may be used for the diagnosis of disorders characterized by expression of PKH, or in assays to monitor patients being treated with PKH or agonists, antagonists, or inhibitors of PKH. Antibodies useful for diagnostic purposes may be prepared in the same manner as described above for therapeutics. Diagnostic assays for PKH include methods which utilize the antibody and a label to detect PKH in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring PKH, including ELISAs, RIAs, and FACS, are known in the art and provide a basis for diagnosing altered or abnormal levels of PKH expression. Normal or standard values for PKH expression are established by combining body fluids or cell extracts taken from normal mammalian subjects, preferably human, with antibody to PKH under conditions suitable for complex formation. The amount of standard complex formation may be quantitated by various methods, preferably by photometric means. Quantities of PKH expressed in subject, samples from biopsied tissues are compared with the standard values. Deviation between standard and subject values establishes the parameters for diagnosing disease.

In another embodiment of the invention, the polynucleotides encoding PKH may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of PKH may be correlated with disease. The diagnostic assay may be used to determine absence, presence, and excess expression of PKH, and to monitor regulation of PKH levels during therapeutic intervention.

In one aspect, hybridization with PCR probes which are capable of detecting polynucleotide sequences, including genomic sequences, encoding PKH or closely related molecules may be used to identify nucleic acid sequences which encode PKH. The specificity of the probe, whether it is made from a highly specific region, e.g., the 5' regulatory region, or from a less specific region, e.g., a conserved motif, and the stringency of the hybridization or amplification (maximal, high, intermediate, or low), will determine whether the probe identifies only naturally occurring sequences encoding PKH, allelic variants, or related sequences.

Probes may also be used for the detection of related sequences, and should preferably have at least 50% sequence identity to any of the PKH encoding sequences. The hybridization probes of the subject invention may be DNA or RNA and may be derived from the sequence of SEQ ID NO: 10–18 or from genomic sequences including promoters, enhancers, and introns of the PKH gene.

Means for producing specific hybridization probes for DNAs encoding PKH include the cloning of polynucleotide sequences encoding PKH or PKH derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}$P or $^{35}$S, or by enzymatic labels, such as alkaline phosphatase coupled to the probe via avidin/biotin coupling systems, and the like.

Polynucleotide sequences encoding PKH may be used for the diagnosis of disorders associated with expression of PKH. Examples of such disorders include, but are not limited to, cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; autoimmune/inflammatory disorders such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermnatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma; and reproductive disorders including disorders of prolactin production; infertility, including tubal disease, ovulatory defects, and endometriosis; disruptions of the estrous cycle, disruptions of the menstrual cycle, polycystic ovary syndrome, ovarian hyperstimulation syndrome, endometrial and ovarian tumors, uterine fibroids, autoimmune disorders, ectopic pregnancies, and teratogenesis; cancer of the breast, fibrocystic breast disease, and galactorrhea; disruptions of spermatogenesis, abnormal sperm physiology, cancer of the testis, cancer of the prostate, benign prostatic hyperplasia, prostatitis, Peyronie's disease, impotence, carcinoma of the male breast, and gynecomastia. The polynucleotide sequences encoding PKH may be used in Southern or northern analysis, dot blot, or other membrane-based technologies; in PCR technologies; in dipstick, pin, and multiformat ELISA-like assays; and in microarrays utilizing fluids or tissues from patients to detect altered PKH expression. Such qualitative or quantitative methods are well known in the art.

In aparticular aspect, the nucleotide sequences encoding PKH may be useful in assays that detect the presence of associated disorders, particularly those mentioned above. The nucleotide sequences encoding PKH may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered in comparison to a control sample then the presence of altered levels of nucleotide sequences encoding PKH in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of PKH, a normal or standard profile for expression is established. This may be accomplished by combining body fluids or cell extracts taken from normal subjects, either animal or human, with a sequence, or a fragment thereof, encoding PKH, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of an abnormal amount of transcript (either under- or overexpressed) in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding PKH may involve the use of PCR. These oligomers may be chemically synthesized, generated enzymatically, or produced in vitro. Oligomers will preferably contain a fragment of a polynucleotide encoding PKH, or a fragment of a polynucleotide complementary to the polynucleotide encoding PKH, and will be employed under optimized conditions for identification of a specific gene or condition. Oligomers may also be employed under less stringent conditions for detection or quantitation of closely related DNA or RNA sequences.

Methods which may also be used to quantitate the expression of PKH include radiolabeling or biotinylating nucleotides, coamplification of a control nucleic acid, and interpolating results from standard curves. (See, e.g., Melby, P. C. et al. (1993) J. Immunol. Methods 159:235–244; Duplaa, C. et al. (1993) Anal. Biochem. 212: 229–236.) The speed of quantitation of multiple samples may be accelerated by running the assay in an ELISA format where the oligomer of interest is presented in various dilutions and a spectrophotometric or calorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously and to identify genetic variants, mutations, and polymorphisms. This information may be used to determine gene function, to understand the genetic basis of a disorder, to diagnose a disorder, and to develop and monitor the activities of therapeutic agents.

Microarrays may be prepared, used, and analyzed using methods known in the art. (See, e.g., Brennan, T. M. et al. (1995) U.S. Pat. No. 5,474,796; Schena, M. et al. (1 996) Proc. Natl. Acad. Sci. 93:10614–10619; Baldeschweiler et al. (1995) PCT application WO95/251116; Shalon, D. et al. (1995) PCT application WO95/35505; Heller, R. A. et al. (1997) Proc. Natl. Acad. Sci. 94:2150–2155; and Heller, M. J. et al. (1997) U.S. Pat. No. 5,605,662.)

In another embodiment of the invention, nucleic acid sequences encoding PKH may be used to generate hybridization probes useful in mapping the naturally occurring genomic sequence. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries. (See, e.g., Harrington, J. J. et al. (1997) Nat. Genet. 15:345–355; Price, C. M. (1993) Blood Rev. 7:127–134; and Trask, B. J. (1991) Trends Genet. 7:149–154.)

Fluorescent in situ hybridization (FISH) may be correlated with other physical chromosome mapping techniques and genetic map data. (See, e.g., Heinz-Ulrich, et al. (1995) in Meyers, supra, pp. 965–968.) Examples of genetic map data can be found in various scientific journals or at the Online Mendelian Inheritance in Man (OMIM) site. Correlation between the location of the gene encoding PKH on a physical chromosomal map and a specific disorder, or a predisposition to a specific disorder, may help define the region of DNA associated with that disorder. The nucleotide sequences of the invention may be used to detect differences in gene sequences among normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms by physical mapping. This provides valuable information to investigators searching for disease genes using positional cloning or other gene discovery techniques. Once the disease or syndrome has been crudely localized by genetic linkage to a particular genomic region, e.g., ataxia-telangiectasia to 11q22–23, any sequences mapping to that area may represent associated or regulatory genes for further investigation. (See, e.g., Gatti, R. A. et al. (1988) Nature 336:577–580.) The nucleotide sequence of the subject invention may also be used to detect differences in the chromosomal location due to translocation, inversion, etc., among normal, carrier, or affected individuals.

In another embodiment of the invention, PKH, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between PKH and the agent being tested may be measured.

Another technique for drug screening provides for high throughput screening of compounds having suitable binding affinity to the protein of interest. (See, e.g., Geysen, et al. (1984) PCT application WO84/03564.) In this method, large numbers of different small test compounds are synthesized on a solid substrate. The test compounds are reacted with PKH, or fragments thereof, and washed. Bound PKH is then detected by methods well known in the art. Purified PKH can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding PKH specifically compete with a test compound for binding PKH. In this manner, antibodies can be used to detect the presence of any peptide which shares one or more antigenic determinants with PKH.

In additional embodiments, the nucleotide sequences which encode PKH may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. Construction of cDNA Libraries

RNA was purchased from Clontech or isolated from tissues described in Table 4. Some tissues were homogenized and lysed in guanidinium isothiocyanate, while others were homogenized and lysed in phenol or in a suitable mixture of denaturants, such as TRIZOL reagent (Life Technologies), a monophasic solution of phenol and guanidine isothiocyanate. The resulting lysates were centrifiuged over CsCl cushions or extracted with chloroform. RNA was precipitated from the lysates with either isopropanol or sodium acetate and ethanol, or by other routine methods.

Phenol extraction and precipitation of RNA were repeated as necessary to increase RNA purity. In some cases, RNA was treated with DNase. For most libraries, poly(A+) RNA was isolated using oligo d(T)-coupled paramagnetic particles (Promega), OLIGOTEX latex particles (QIAGEN, Valencia Calif.), or an OLIGOTEX mRNA purification kit (QIAGEN). Alternatively, RNA was isolated directly from tissue lysates using other RNA isolation kits, e.g., the POLY(A)PURE mRNA purification kit (Ambion, Austin Tex.).

In some cases, Stratagene was provided with RNA and constructed the corresponding cDNA libraries. Otherwise, cDNA was synthesized and cDNA libraries were constructed with the UNIZAP vector system (Stratagene) or SUPERSCRIPT plasmid system (Life Technologies), using the recommended procedures or similar methods known in the art. (See, e.g., Ausubel, 1997, supra, units 5.1–6.6). Reverse transcription was initiated using oligo d(T) or random primers. Synthetic oligonucleotide adapters were ligated to double stranded cDNA, and the cDNA was digested with the appropriate restriction enzyme or enzymes. For most libraries, the cDNA was size-selected (300–1000 bp) using SEPHACRYL S1000, SEPHAROSE CL2B, or SEPHAROSE CL4B column chromatography (Amersham Pharmacia Biotech) or preparative agarose gel electrophoresis. cDNAs were ligated into compatible restriction enzyme sites of the polylinker of a suitable plasmid, e.g., PBLUESCRIPT plasmid (Stratagene), PSPORT1 plasmid (Life Technologies), or pINCY (Incyte Pharmaceuticals, Palo Alto Calif.). Recombinant plasmids were transformed into competent E. coli cells including XL1-Blue, XL1-Blue MRF, or SOLR from Stratagene or DH5α, DH10B, or ELECTROMAX DH10B from Life Technologies.

II. Isolation of cDNA Clones

Plasmids were recovered from host cells by in vivo excision, using the UNIZAP vector system (Stratagene) or cell lysis. Plasmids were purified using at least one of the following: a Magic or WIZARD Minipreps DNA purification system (Promega); an AGTC Miniprep purification kit (Edge Biosystems, Gaithersburg Md.); and QIAWELL 8 Plasmid, QIAWELL 8 Plus Plasmid, QIAWELL 8 Ultra. plasmid purification systems or the R.E.A.L. Prep 96 plasmid kit from QIAGEN. Following precipitation, plasmids were resuspended in 0.1 ml of distilled water and stored, with or without lyophilization, at 4° C.

Alternatively, plasmid DNA was amplified from host cell lysates using direct link PCR in a high-throughput format (Rao, V.B. (1994) Anal. Biochem. 216:1–14). Host cell lysis and thermal cycling steps were carried out in a single reaction mixture. Samples were processed and stored in 384-well plates, and the concentration of amplified plasmid DNA was quantified fluorometrically using PICOGREEN dye (Molecular Probes, Eugene Ore.) and a Fluoroskan II fluorescence scanner (Labsystems Oy, Helsinki, Finland).

III. Sequencing and Analysis

The-cDNAs were prepared for sequencing using the ABI CATALYST 800 (Perkin-Elmer) or the HYDRA microdispenser (Robbins Scientific) or MICROLAB 2200 (Hamilton) systems in combination with the PTC-200 thermal cyclers (MJ Research). The cDNAs were sequenced using the ABI PRISM 373 or 377 sequencing systems (Perkin-Elmer) and standard ABI protocols, base calling software, and kits. In one alternative, cDNAs were sequenced using the MEGABACE 1000 DNA sequencing system (Molecular Dynamics). In another alternative, the cDNAs were amplified and sequenced using the ABI PRISM BIGDYE Terminator cycle sequencing ready reaction kit (Perkin-Elmer). In yet another alternative, cDNAs were sequenced using solutions and dyes from Amersham Pharmacia Biotech. Reading frames for the ESTs were determined using standard methods (reviewed in Ausubel, 1997, supra, unit 7.7). Some of the cDNA sequences were selected for extension using the techniques disclosed in Example V.

The polynucleotide sequences derived from cDNA, extension, and shotgun sequencing were assembled and analyzed using a combination of software programs which utilize algorithms well known to those skilled in the art. Table 5 summarizes the software programs, descriptions, references, and threshold parameters used. The first column of Table 5 shows the tools, programs, and algorithms used, the second column provides a brief description thereof, the third column presents the references which are incorporated by reference herein, and the fourth column presents, where applicable, the scores, probability values, and other parameters used to evaluate the strength of a match between two sequences (the higher the probability the greater the homology). Sequences were analyzed using MACDNASIS PRO software (Hitachi Software Engineering, South San Francisco Calif.) and LASERGENE software (DNASTAR).

The polynucleotide sequences were validated by removing vector, linker, and polyA sequences and by masking ambiguous bases, using algorithms and programs based on BLAST, dynamic programing, and dinucleotide nearest neighbor analysis. The sequences were then queried against a selection of public databases such as GenBank primate, rodent, mammalian, vertebrate, and eukaryote databases, and BLOCKS to acquire annotation, using programs based on BLAST, FASTA, and BLIMPS. The sequences were assembled into full length polynucleotide sequences using programs based on Phred, Phrap, and Consed, and were screened for open reading frames using programs based on GeneMark, BLAST, and FASTA. The full length polynucleotide sequences were translated to derive the corresponding full length amino acid sequences, and these full length sequences were subsequently analyzed by querying against databases such as the GenBank databases (described above), SwissProt, BLOCKS, PRINTS, PFAM, and Prosite.

The programs described above for the assembly and analysis of full length polynucleotide and amino acid sequences were also used to identify polynucleotide sequence fragments from SEQ ID NO: 10–18. Fragments from about 20 to about 4000 nucleotides which are useful in hybridization and amplification technologies were described in The Invention section above.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; Ausubel, 1995, supra, ch.4 and 16.)

Analogous computer techniques applying BLAST were used to search for identical or related molecules in nucleotide databases such as GenBank or LIFESEQ database (Incyte Pharmaceuticals). This analysis is much faster than multiple membrane-based hybridizations. In addition, the sensitivity of the computer search can be modified to determine whether any particular match is categorized as exact or similar. The basis of the search is the product score, which is defined as:

$$\frac{\% \text{ sequence identity} \times \text{maximum BLAST score}}{100}$$

The product score takes into account both the degree of similarity between two sequences and the length of the sequence match. For example, with a product score of 40, the match will be exact within a 1% to 2% error, and, with a product score of 70, the match will be exact. Similar molecules are usually identified by selecting those which show product scores between 15 and 40, although lower scores may identify related molecules.

The results of northern analyses are reported as a percentage distribution of libraries in which the transcript encoding PKH occurred. Analysis involved the categorization of cDNA libraries by organ/tissue and disease. The organ/tissue categories included cardiovascular, dermatologic, developmental, endocrine, gastrointestinal, hematopoietic/immune, musculoskeletal, nervous, reproductive, and urologic. The disease/condition categories included cancer, inflammation/trauma, cell proliferation, neurological, and pooled. For each category, the number of libraries expressing the sequence of interest was counted and divided by the total number of libraries across all categories. Percentage values of tissue-specific and disease- or condition-specific expression are reported in Table 3.

V. Extension of PKH Encoding Polynucleotides

The full length nucleic acid sequence of SEQ ID NO: 10–18 was produced by extension of an appropriate fragment of the full length molecule using oligonucleotide primers designed from this fragment. One primer was synthesized to initiate 5' extension of the known fragment, and the other primer, to initiate 3' extension of the known fragment. The initial primers were designed using OLIGO 4.06 software (National Biosciences), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries were used to extend the sequence. If more than one extension was necessary or desired, additional or nested sets of primers were designed.

High fidelity amplification was obtained by PCR using methods well known in the art. PCR was performed in 96-well plates using the PTC-200 thermal cycler (MJ Research, Inc.). The reaction mix contained DNA template, 200 nmol of each primer, reaction buffer containing $Mg^{2+}$, $(NH_4)_2SO_4$, and β-mercaptoethanol, Taq DNA polymerase (Amersham Pharmacia Biotech), ELONGASE enzyme (Life Technologies), and Pfu DNA polymerase (Stratagene), with the following parameters for primer pair PCI A and PCI B: Step 1: 94° C., 3 min; Step 2: 94° C., 15 sec; Step 3: 60° C., 1 min; Step 4: 68° C., 2 min; Step 5: Steps 2, 3, and 4 repeated 20 times; Step 6: 68° C., 5 min; Step 7: storage at 4° C. In the alternative, the parameters for primer pair T7 and SK+ were as follows: Step 1: 94° C., 3 min; Step 2: 94° C., 15 sec; Step 3: 57° C., 1 min; Step 4: 68° C., 2 min; Step 5: Steps 2, 3, and 4 repeated 20 times; Step 6: 68° C., 5 min; Step 7: storage at 4° C.

The concentration of DNA in each well was determined by dispensing 100 μl PICOGREEN quantitation reagent (0.25% (v/v) PICOGREEN; Molecular Probes, Eugene Oreg.) dissolved in 1X TE and 0.5 μl of undiluted PCR product into each well of an opaque fluorimeter plate (Coming Costar, Acton Mass.), allowing the DNA to bind to the reagent. The plate was scanned in a Fluoroskan II (Labsystems Oy, Helsinki, Finland) to measure the fluorescence of the sample and to quantify the concentration of DNA. A 5 μl to 10 μl aliquot of the reaction mixture was analyzed by electrophoresis on a 1% agarose mini-gel to determine which reactions were successfutl in extending the sequence.

The extended nucleotides were desalted and concentrated, transferred to 384-well plates, digested with CviJI cholera virus endonuclease (Molecular Biology Research, Madison Wis.), and sonicated or sheared prior to religation into pUC 18 vector (Amersham Pharmacia Biotech). For shotgun sequencing, the digested nucleotides were separated on low concentration (0.6 to 0.8%) agarose gels, fragments were excised, and agar digested with Agar ACE (Promega). Extended clones were religated using T4 ligase (New England Biolabs, Beverly Mass.) into pUC 18 vector (Amersham Pharmacia Biotech), treated with Pfu DNA polymerase (Stratagene) to fill-in restriction site overhangs, and transfected into competent E. coli cells. Transformed cells were selected on antibiotic-containing media, individual colonies were picked and cultured overnight at 37° C. in 384-well plates in LB/2xcarb liquid media.

The cells were lysed, and DNA was amplified by PCR using Taq DNA polymerase (Amersham Pharmacia Biotech) and Pfu DNA polymerase (Stratagene) with the following parameters: Step 1: 94° C., 3 min; Step 2: 94° C., 15 sec; Step 3: 60° C., 1 min; Step 4: 72° C., 2 min; Step 5: steps 2, 3, and step 4 repeated 29 times; Step 6: 72° C., 5 min; Step 7: storage at 4° C. DNA was quantified by PICOGREEN reagent (Molecular Probes) as described above. Samples with low DNA recoveries were reamplified using the same conditions as described above. Samples were diluted with 20% dimethysulphoxide (1:2, v/v), and sequenced using DYENAMIC energy transfer sequencing primers and the DYENAMIC DIRECT kit (Amersham Pharmacia Biotech) or the ABI PRISM BIGDYE Terminator cycle sequencing ready reaction kit (Perkin-Elmer).

In like manner, the nucleotide sequence of SEQ ID NO: 10–18 is used to obtain 5' regulatory sequences using the procedure above, oligonucleotides designed for such extension, and an appropriate genomic library.

VI. Labeling and Use of Individual Hybridization Probes

Hybridization probes derived from SEQ ID NO: 10–18 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 software (National Biosciences)

and labeled by combining 50 pmol of each oligomer, 250 μCi of [λ-$^{32}$P] adenosine triphosphate (Amersham Pharmacia Biotech), and T4 polynucleotide kinase (DuPont NEN, Boston Mass.). The labeled oligonucleotides are substantially purified using a SEPHADEX G-25 superfine size exclusion dextran bead column (Amersham Pharmacia Biotech). An aliquot containing 10$^7$ counts per minute of the labeled probe is used in a typical membrane-based hybridization analysis of human genomic DNA digested with one of the following endonucleases: Ase I, Bgl II, Eco RI, Pst I, XbaI, or Pvu II (DuPont NEN).

The DNA from each digest is fractionated on a 0.7% agarose gel and transferred to nylon membranes (NYTRAN PLUS, Schleicher & Schuell, Durham N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT-AR film (Eastman Kodak, Rochester N.Y.) is exposed to the blots hybridization patterns are compared visually.

VII. Microarrays

A chemical coupling procedure and an ink jet device can be used to synthesize array elements on the surface of a substrate. (See, e.g., Baldeschweiler, supra.) An array analogous to a dot or slot blot may also be used to arrange and link elements to the surface of a substrate using thermal, UV, chemical, or mechanical bonding procedures. A typical array may be produced by hand or using available methods and machines and contain any appropriate number of elements. After hybridization, nonhybridized probes are removed and a scanner used to determine the levels and patterns of fluorescence. The degree of complementarity and the relative abundance of each probe which hybridizes to an element on the microarray may be assessed through analysis of the scanned images.

Full-length cDNAs, Expressed Sequence Tags (ESTs), or fragments thereof may comprise the elements of the microarray. Fragments suitable for hybridization can be selected using software well known in the art such as LASERGENE software (DNASTAR). Full-length cDNAs, ESTs, or fragments thereof corresponding to one of the nucleotide sequences of the present invention, or selected at random from a cDNA library relevant to the present invention, are arranged on an appropriate substrate, e.g., a glass slide. The cDNA is fixed to the slide using, e.g., UV cross-linking, followed by thermal and chemical treatments and subsequent drying. (See, e.g., Schena, M. et al. (1995) Science 270:467–470; Shalon, D. et al. (1996) Genome Res. 6:639–645.) Fluorescent probes are prepared and used for hybridization to the elements on the substrate. The substrate is analyzed by procedures described above.

VIII. Complementary Polynucleotides

Sequences complementary to the PKH-encoding sequences, or any parts thereof, are used to detect, decrease, or inhibit expression of naturally occurring PKH. Although use of oligonucleotides comprising from about 15 to 30 base pairs is described, essentially the same procedure is used with smaller or with larger sequence fragments. Appropriate oligonucleotides are designed using OLIGO 4.06 software (National Biosciences) and the coding sequence of PKH. To inhibit transcription, a complementary oligonucleotide is designed from the most unique 5' sequence and used to prevent promoter binding to the coding sequence. To inhibit translation, a complementary oligonucleotide is designed to prevent ribosomal binding to the PKH-encoding transcript.

IX. Expression of PKH

Expression and purification of PKH is achieved using bacterial or virus-based expression systems. For expression of PKH in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts, e.g., BL21 (DE3). Antibiotic resistant bacteria express PKH upon induction with isopropyl beta-D-thiogalactopyranoside (IPTG). Expression of PKH in eukaryotic cells is achieved by infecting insect or mammalian cell lines with recombinant *Autographica californica* nuclear polyhedrosis virus (AcMNPV), commonly known as baculovirus. The nonessential polyhedrin gene of baculovirus is replaced with cDNA encoding PKH by either homologous recombination or bacterial-mediated transposition involving transfer plasmid intermediates. Viral infectivity is maintained and the strong polyhedrin promoter drives high levels of cDNA transcription. Recombinant baculovirus is used to infect *Spodoptera frugiperda* (Sf9) insect cells in most cases, or human hepatocytes, in some cases. Infection of the latter requires additional genetic modifications to baculovirus. (See Engelhard, E. K. et al. (1994) Proc. Natl. Acad. Sci. USA 91:3224–3227; Sandig, V. et al. (1996) Hum. Gene Ther. 7:1937–1945.)

In most expression systems, PKH is synthesized as a fusion protein with, e.g., glutathione S-transferase (GST) or a peptide epitope tag, such as FLAG or 6-His, permitting rapid, single-step, affinity-based purification of recombinant fusion protein from crude cell lysates. GST, a 26-kilodalton enzyme from *Schistosoma jaronicum*, enables the purification of fusion proteins on immobilized glutathione under conditions that maintain protein activity and antigenicity (Amersham Pharmacia Biotech). Following purification, the GST moiety can be proteolytically cleaved from PKH at specifically engineered sites. FLAG, an 8-amino acid peptide, enables immunoaffinity purification using commercially available monoclonal and polyclonal anti-FLAG antibodies (Eastman Kodak). 6-His, a stretch of six consecutive histidine residues, enables purification on metal-chelate resins (QIAGEN). Methods for protein expression and purification are discussed in Ausubel (1995, supra, ch 10 and 16). Purified PKH obtained by these methods can be used directly in the following activity assay.

X. Demonstration of PKH Activity

An assay for PKH activity measures the phosphorylation of a substrate in the presence of gamma-labeled $^{32}$P-ATP. PKH is incubated with an appropriate substrate and $^{32}$P-ATP in a buffered solution. $^{32}$P-labeled product is separated from free $^{32}$P-ATP by gel electrophoresis or chromatographic procedures, and the incorporated $^{32}$P is quantified by phosphoimage analysis or scintillation counter. The amount of $^{32}$P detected is proportional to the activity of PKH in this assay. The specific amino acid residue phosphorylated by PKH may be determined by phosphoamino acid analysis of the labeled, hydrolyzed protein.

XI. Functional Assays

PKH function is assessed by expressing the sequences encoding PKH at physiologically elevated levels in mammalian cell culture systems. cDNA is subcloned into a mammalian expression vector containing a strong promoter that drives high levels of cDNA expression. Vectors of choice include PCMV SPORT (Life Technologies) and pCR3.1 (Invitrogen, Carlsbad Calif.), both of which contain the cytomegalovirus promoter. 5–10 μg of recombinant vector are transiently transfected into a human cell line, preferably of endothelial or hematopoietic origin, using either liposome formulations or electroporation. 1–2 μg of an additional plasmid containing sequences encoding a marker protein are co-transfected. Expression of a marker protein provides a means to distinquish transfected cells from nontransfected cells and is a reliable predictor of cDNA expression from the recombinant vector. Marker proteins of choice include, e.g., Green Fluorescent Protein (GFP; Clontech), CD64, or a CD64-GFP fusion protein. Flow cytometry (FCM), an automated, laser optics-based technique, is used to identify transfected cells expressing GFP or CD64-GFP, and to evaluate properties, for example, their apoptotic state. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994) *Flow Cytometgy*, Oxford, New York N.Y.

The influence of PKH on gene expression can be assessed using highly purified populations of cells transfected with sequences encoding PKH and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success N.Y.). mRNA can be purified from the cells using methods well known by those of skill in the art. Expression of mRNA encoding PKH and other genes of interest can be analyzed by northern analysis or microarray techniques.

XII. Production of PKH Specific Antibodies

PKH substantially purified using polyacrylamide gel electrophoresis (PAGE; see, e.g., Harrington, M. G. (1990) Methods Enzymol. 182:488–495), or other purification techniques, is used to immunize rabbits and to produce antibodies using standard protocols.

Alternatively, the PKH amino acid sequence is analyzed using LASERGENE software (DNASTAR) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel, 1995, supra, ch. 11.)

Typically, oligopeptides 15 residues in length are synthesized using an ABI 431A Peptide synthesizer (Perkin-Elmer) using fmoc-chemistry and coupled to KLH (Sigma-Aldrich, St. Louis Mo.) by reaction with N-maleimidobenzoyl-N-hydroxysuccinimide ester (MBS) to increase immunogenicity. (See, e.g., Ausubel, 1995, supra.) Rabbits are immunized with the oligopeptide-KLH complex in complete Freund's adjuvant. Resulting antisera are tested for antipeptide activity by, for example, binding the peptide to plastic, blocking with 1% BSA, reacting with rabbit antisera, washing, and reacting with radio-iodinated goat anti-rabbit IgG.

XIII. Purification of Naturally Occurring PKH Using Specific Antibodies

Naturally occurring or recombinant PKH is substantially purified by immunoaffinity chromatography using antibodies specific for PKH. An immunoaffinity column is constructed by covalently coupling anti-PKH antibody to an activated chromatographic resin, such as CNBr-activated SEPHAROSE (Amersham Pharnacia Biotech). After the coupling, the resin is blocked and washed according to the manufacturer's instructions.

Media containing PKH are passed over the immunoaffinity column, and the column is washed under conditions that allow the preferential absorbance of PKH (e.g., high ionic strength buffers in the presence of detergent). The column is eluted under conditions that disrupt antibody/PKH binding (e.g., a buffer of pH 2 to pH 3, or a high concentration of a chaotrope, such as urea or thiocyanate ion), and PKH is collected.

XIV. Identification of Molecules Which Interact with PKH

PKH, or biologically active fragments thereof, are labeled with $^{125}$I Bolton-Hunter reagent. (See, e.g., Bolton et al. (1973) Biochem. J. 133:529.) Candidate molecules previously arrayed in the wells of a multi-well plate are incubated with the labeled PKH, washed, and any wells with labeled PKH complex are assayed. Data obtained using different concentrations of PKH are used to calculate values for the number, affinity, and association of PKH with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

TABLE 1

| Amino Acid SEQ ID NO: | Nucleotide SEQ ID NO: | Clone ID | Library | Fragments |
|---|---|---|---|---|
| 1 | 10 | 119819 | MUSCNOT01 | 119819H1 (MUSCNOT01), 1476434H1 (CORPNOT02), 1719355H1 (BLADNOT06), 3016364F6 (MUSCNOT07), 3373249F6 (CONNTUT05) |

TABLE 1-continued

| Amino Acid SEQ ID NO: | Nucleotide SEQ ID NO: | Clone ID | Library | Fragments |
|---|---|---|---|---|
| 2 | 11 | 132750 | BMARNOT02 | 132750H1 and 132750X335D1 (BMARNOT02), 287300R1 (EOSIHET02), 1271292F1 (TESTTUT02), 3343321H1 (SPLNNOT09) |
| 3 | 12 | 507669 | TMLR3DT01 | 101010R6 (ADRENOT01), 507669H1 and 507669R6 (TMLR3DT01), 697674H1 (SYNORAT03), 851624T1 (NGANNOT01), 1270195F7 (BRAINOT09) |
| 4 | 13 | 1439938 | THYRNOT03 | 814363X11 (OVARTUT01), 822246X13 (KERANOT02), 1439938H1 (THYRNOT03), 3365318F6 (PROSBPT02) |
| 5 | 14 | 1447427 | PLACNOT02 | 712366R6 (SYNORAT04), 1447427H1 (PLACNOT02), 2179842F6 (SININOT01), 2697460F6 (UTRSNOT12) |
| 6 | 15 | 1567782 | UTRSNOT05 | 1567782H1 and 1567786F6 (UTRSNOT05), 2289257X42F1 (BRAINON01), 2839231T6 (DRGLNOT01), SAFB00259F1 |
| 7 | 16 | 2295842 | BRSTNOT05 | 606173H1 (BRSTTUT01), 865560R1 (BRAITUT03), 1441018F6 (THYRNOT03), 1706132T6 (DUODNOT02), 1811824F6 (PROSTUT12), 2223155H1 (LUNGNOT18), 2295842H1 (BRSTNOT05) |
| 8 | 17 | 2605059 | LUNGTUT07 | 381188R6 (HYPONOB01), 381188T6 (HYPONOB01), 691185T6 (LUNGTUT02), 1824201F6 (GBLATUT01), 2605059F6, 2605059H1 and 2605059X304F1 (LUNGTUT07) |
| 9 | 18 | 3000825 | TLYMNOT06 | 2015630F6 (ADRENOT07), 3000825F6 and 3000825H1 (TLYMNOT06) |

TABLE 2

| Amino Acid Seq ID NO: | Amino Acid Residues | Potential Phosphorylation Sites | Signature Sequence | Identification | Analytical Methods |
|---|---|---|---|---|---|
| 1 | 297 | S285 T29 S197 S202 S225 S285 | A117–L295 | SR protein-specific kinase | PFAM, BLAST, BLOCKS, MOTIFS |
| 2 | 287 | S283 T106 T179 S194 S274 T69 T184 S233 S270 | S31–T284 | protein kinase homolog | PFAM, BLOCKS, PRINTS, BLAST, MOTIFS |
| 3 | 346 | S7 T105 S160 T232 T244 T282 S329 T336 S214 T255 Y231 | E125–D333 | tyrosine kinase | PFAM, BLAST, BLOCKS, PRINTS, PROFILESCAN, MOTIFS |
| 4 | 90 | S60 S9 S62 | F28–R78 | protein kinase homolog | PFAM, BLOCKS, BLAST, MOTIFS |
| 5 | 327 | S96 T210 S277 T40 S137 S179 T273 Y178 Y310 | Y11–N235 | protein kinase homolog | PFAM, BLOCKS, PRINTS, BLAST, MOTIFS |
| 6 | 345 | S327 S23 S41 S48 S123 S219 T319 T166 S175 Y30 | Y4–I226 | serine/threonine- and tyrosine-specific protein kinase, Nek1 | PFAM, BLAST, BLOCKS, PRINTS, PROFILESCAN, MOTIFS |
| 7 | 424 | T97 S218 S298 T389 S413 T54 T62 T89 T109 S112 S151 S223 S229 S286 S318 | D202–V412 | protein kinase homolog | PFAM, BLOCKS, PRINTS, BLAST, MOTIFS |
| 8 | 99 | | | cdc2+/CDC28-related protein kinase | BLAST |
| 9 | 138 | T91 T24 T57 T91 T14 | R72–V101 | serine/threonine protein kinase | PFAM, BLAST, MOTIFS |

TABLE 3

| Nucleotide Seq ID NO: | Tissue Expression (Fraction of Total) | Disease or Condition (Fraction of Total) | Vector |
|---|---|---|---|
| 10 | Nervous (0.400) Musculoskeletal (0.200) Cardiovascular (0.100) | Cancer (0.500) Neurological (0.300) | pBluescript |
| 11 | Reproductive (0.316) Hematopoietic/Immune (0.211) Gastrointestinal (0.158) | Inflammation (0.421) Cancer (0.368) | pBluescript |
| 12 | Hematopoietic/Immune (0.514) Gastrointestinal (0.189) Reproductive (0.081) | Inflammation (0.595) Cancer (0.243) | pBluescript |
| 13 | Reproductive (0.375) Developmental (0.125) Endocrine (0.125) | Cancer (0.375) Inflammation (0.250) | pINCY |
| 14 | Reproductive (0.346) Nervous (0.269) Hematopoietic/Immune (0.231) | Cancer (0.462) Inflammation (0.385) | pINCY |
| 15 | Nervous (0.500) Developmental (0.167) Musculoskeletal (0.167) | Cancer (0.833) Inflammation (0.333) | pINCY |
| 16 | Reproductive (0.290) Gastrointestinal (0.145) Nervous (0.130) | Cancer (0.420) Inflammation (0.362) | pSPORT1 |

TABLE 3-continued

| Nucleotide Seq ID NO: | Tissue Expression (Fraction of Total) | Disease or Condition (Fraction of Total) | Vector |
|---|---|---|---|
| 17 | Nervous (0.250) Gastrointestinal (0.167) Hematopoietic/Immune (0.167) | Cancer (0.500) Inflammation (0.250) | pINCY |
| 18 | Endocrine (0.333) Hematopoietic/Immune (0.333) Reproductive (0.333) | Inflammation (0.667) Cancer (0.333) | pINCY |

TABLE 4

| Nucleotide SEQ ID NO: | Library | Library Comment |
|---|---|---|
| 10 | MUSCNOT01 | Library was constructed at Stratagene (STR937209), using RNA isolated from the skeletal muscle tissue of a patient with malignant hyperthermia. |
| 11 | BMARNOT02 | Library was constructed using RNA isolated from the bone marrow of 24 male and female Caucasian donors, 16 to 70 years old. (RNA came from Clontech.) |
| 12 | TMLR3DT02 | Library was constructed using RNA isolated from non-adherent peripheral blood mononuclear cells collected from a pool of male and female donors. Cells from each donor were purified on Ficoll Hypaque, then co-cultured for 72 hours. The cells were pooled, washed once in PBS, lysed in a buffer containing GuSCN, and spun through CsCl to obtain RNA. PolyA RNA was isolated using a Qiagen Oligotex kit. |
| 13 | THYRNOT03 | Library was constructed using RNA isolated from thyroid tissue removed from the left thyroid of a 28-year-old Caucasian female during a complete thyroidectomy. Pathology indicated a small nodule of adenomatous hyperplasia present in the left thyroid. Pathology for the associated tumor tissue indicated dominant follicular adenoma, forming a well-encapsulated mass in the left thyroid. |
| 14 | PLACNOT02 | Library was constructed using RNA isolated from the placental tissue of a Hispanic female fetus, who was prematurely delivered at 21 weeks' gestation. Serologies of the mother's blood were positive for cytomegalovirus. |
| 15 | UTRSNOT05 | Library was constructed using RNA isolated from the uterine tissue of a 45-year-old Caucasian female during a total abdominal hysterectomy and total colectomy. Pathology for the associated tumor tissue indicated multiple leiomyomas of the myometrium. |
| 16 | BRSTNOT05 | Library was constructed using RNA isolated from breast tissue removed from a 58-year-old Caucasian female during a unilateral extended simple mastectomy. Pathology for the associated tumor tissue indicated multicentric invasive grade 4 lobular carcinoma. Family history included breast and prostate cancer. |
| 17 | LUNCTUT07 | Library was constructed using RNA isolated from lung tumor tissue removed from the upper lobe of a 50-year-old Caucasian male during segmental lung resection. Pathology indicated an invasive grade 4 squamous cell adenocarcinoma. Patient history included tobacco use. Family history included skin cancer. |
| 18 | TLYMNOT06 | Library was constructed using RNA isolated from activated Th2 cells. These cells were differentiated from umbilical cord CD4 T cells with IL-4 in the presence of anti-IL-12 antibodies and B7-transfected COS cells, and then activated for six hours with anti-CD3 and anti-CD28 antibodies. |

TABLE 5

| Program | Description | Reference | Parameter Threshold |
|---|---|---|---|
| ABI FACTURA | A program that removes vector sequences and masks ambiguous bases in nucleic acid sequences. | Perkin-Elmer Applied Biosystems, Foster City, CA. | |
| ABI/ PARACEL FDF | A Fast Data Finder useful in comparing and annotating amino acid or nucleic acid sequences. | Perkin-Elmer Applied Biosystems, Foster City, CA; Paracel Inc., Pasadena, CA. | Mismatch <50% |
| ABI AutoAssembler | A program that assembles nucleic acid sequences. | Perkin-Elmer Applied Biosystems, Foster City, CA. | |
| BLAST | A Basic Local Alignment Search Tool useful in sequence similarity search for amino acid and nucleic acid sequences. BLAST includes five functions: blastp, blastn, blastx, tblastn, and tblastx. | Altschul, S. F. et al. (1990) J. Mol. Biol. 215:403–410; Altschul, S. F. et al. (1997) Nucleic Acids Res. 25:3389–3402. | ESTs: Probability value = 1.0E-8 or less Full Length sequences: Probability value = 1.0E-10 or less |
| FASTA | A Pearson and Lipman algorithm that searches for similarity between a query sequence and a group of sequences of the same type. FASTA comprises as least five functions: fasta, tfasta, fastx, tfastx, and ssearch. | Pearson, W. R. and D. J. Lipman (1988) Proc. Natl. Acad Sci. 85:2444–2448; Pearson, W. R. (1990) Methods Enzymol. 183:63–98; and Smith, T. F. and M. S. Waterman (1981) Adv. Appl. Math. 2:482–489. | ESTs: fasta E value = 1.06E-6 Assembled ESTs: fasta Identity = 95% or greater and Match length = |

TABLE 5-continued

| Program | Description | Reference | Parameter Threshold |
|---|---|---|---|
| | | | 200 bases or greater; fastx E value = 1.0E-8 or less Full Length sequences: fastx score = 100 or greater |
| BLIMPS | A BLocks IMProved Searcher that matches a sequence against those in BLOCKS and PRINTS databases to search for gene families, sequence homology, and structural fingerprint regions. | Henikoff S and J. G. Henikoff, Nucl. Acid Res., 19:6565–72, 1991. J. G. Henikoff and S. Henikoff (1996) Methods Enzymol. 266:88–105; and Attwood, T. K. et al. (1997) J. Chem. Inf. Comput. Sci. 37:417–424. | Score = 1000 or greater; Ratio of Score/Strength = 0.75 or larger; and Probability value = 1.0E-3 or less |
| PFAM | A Hidden Markov Models-based application useful for protein family search. | Krogh, A. et al. (1994) J. Mol. Biol., 235:1501–1531; Sonnhammer, E. L. L. etal. (1988) Nucleic Acids Res. 26:320–322. | Score = 10–50 bits, depending on individual protein families |
| ProfileScan | An algorithm that searches for structural and sequence motifs in protein sequences that match sequence patterns defined in Prosite. | Gribskov, M. et al. (1988) CABIOS 4:61–66; Gribskov, et al. (1989) Methods Enzymol. 183:146–159; Bairoch, A. et al. (1997) Nucleic Acids Res. 25:217–221. | Score = 4.0 or greater |
| Phred | A base-calling algorithm that examines automated sequencer traces with high sensitivity and probability. | Ewing, B. et al. (1998) Genome Res. 8:175–185; Ewing, B. and P. Green (1998) Genome Res. 8:186–194. | |
| Phrap | A Phils Revised Assembly Program including SWAT and CrossMatch, programs based on efficient implementation of the Smith-Waterman algorithm, useful in searching sequence homology and assembling DNA sequences. | Smith, T. F. and M. S. Waterman (1981) Adv. Appl. Math. 2:482–489; Smith, T. F. and M. S. Waterman (1981) J. Mol. Biol. 147:195–197; and Green, P., University of Washington, Seattle, WA. | Score = 120 or greater; Match length = 56 or greater |
| Consed | A graphical tool for viewing and editing Phrap assemblies | Gordon, D. et al. (1998) Genome Res.8:195–202. | |
| SPScan | A weight matrix analysis program that scans protein sequences for the presence of secretory signal peptides. | Nielson, H. et al. (1997) Protein Engineering 10:1–6; Claverie, J. M. and S. Audic (1997) CABIOS 12:431–439. | Score = 5 or greater |
| Motifs | A program that searches amino acid sequences for patterns that matched those defined in Prosite. | Bairoch et al. supra; Wisconsin Package Program Manual, version 9, page M51–59, Genetics Computer Group, Madison, WI. | |

What is claimed is:

1. A purified polypeptide comprising an amino acid sequence selected from the group consisting of:
   a) an amino acid sequence selected from the group consisting of SEQ ID NO:1–9,
   b) a naturally-occurring amino acid sequence having at least 95% sequence identity to the sequence selected from the group consisting of SEQ ID NO:1–2, 4, 6–7 and 9, wherein said amino acid sequence encodes a polypeptide having protein kinase activity,
   c) a biologically-active fragment of the amino acid sequence selected from the group consisting of SEQ ID NO:1–2, 4, 6–7 and 9, wherein said biologically-active fragment encodes a polypeptide having protein kinase activity, and
   d) an immunogenic fragment of the amino acid sequence selected from the group consisting of SEQ ID NO:1–2, 4, 6–7 and 9, wherein said polypeptides is capable of generating antibody that specifically binds to the polypeptide selected from the group consisting of SEQ ID NO:1–2, 4, 6–7 and 9.

2. An isolated polypeptide of claim 1, having a sequence selected from the group consisting of SEQ ID NO:1–9.

3. A composition comprising an effective amount of a polypeptide of claim 1 and a pharmaceutically acceptable carrier.

4. A composition of claim 3, wherein the polypeptide has the sequence selected from the group consisting of SEQ ID NO: 1–9.

* * * * *

SEQUENCE LISTING

<160> NUMBER OF SEQ ID NOS: 18

<210> SEQ ID NO 1
<211> LENGTH: 297
<212> TYPE: PRT
<213> ORGANISM: Homo sapiens
<220> FEATURE: -
<223> OTHER INFORMATION: 119819

<400> SEQUENCE: 1

```
Met Arg Arg Lys Arg Lys Gln Gln Lys Arg Leu Leu Glu Glu Arg
 1               5                  10                  15

Leu Arg Asp Leu Gln Arg Leu Glu Ala Met Glu Ala Ala Thr Gln
                20                  25                  30

Ala Glu Asp Ser Gly Leu Arg Leu Asp Gly Gly Ser Gly Ser Thr
                35                  40                  45

Ser Ser Ser Gly Cys His Pro Gly Gly Ala Arg Ala Gly Pro Ser
                50                  55                  60

Pro Ala Ser Ser Pro Ala Pro Gly Gly Arg Ser Leu Ser
                65                  70                  75

Ala Gly Ser Gln Thr Ser Gly Phe Ser Gly Ser Leu Phe Ser Pro
                80                  85                  90
```

-continued

```
Ala Ser Cys Ser Ile Leu Ser Gly Ser Ser Asn Gln Arg Glu Thr
                 95                 100                 105

Gly Gly Leu Leu Ser Pro Ser Thr Pro Phe Gly Ala Ser Asn Leu
             110                 115                 120

Leu Val Asn Pro Leu Glu Pro Gln Asn Ala Asp Lys Ile Lys Ile
             125                 130                 135

Lys Ile Ala Asp Leu Gly Asn Ala Cys Trp Val His Lys His Phe
             140                 145                 150

Thr Glu Asp Ile Gln Thr Arg Gln Tyr Arg Ala Val Glu Val Leu
             155                 160                 165

Ile Gly Ala Glu Tyr Gly Pro Pro Ala Asp Ile Trp Ser Thr Ala
             170                 175                 180

Cys Met Ala Phe Glu Leu Ala Thr Gly Asp Tyr Leu Phe Glu Pro
             185                 190                 195

His Ser Gly Glu Asp Tyr Ser Arg Asp Glu Asp His Ile Ala His
             200                 205                 210

Ile Val Glu Leu Leu Gly Asp Ile Pro Pro Ala Phe Ala Leu Ser
             215                 220                 225

Gly Arg Tyr Ser Arg Glu Phe Phe Asn Arg Arg Gly Glu Leu Arg
             230                 235                 240

His Ile His Asn Leu Lys His Trp Gly Leu Tyr Glu Val Leu Met
             245                 250                 255

Glu Lys Tyr Glu Trp Pro Leu Glu Gln Ala Thr Gln Phe Ser Ala
             260                 265                 270

Phe Leu Leu Pro Met Asn Glu Tyr Ile Pro Glu Lys Arg Ala Ser
             275                 280                 285

Ala Arg Asp Cys Leu Gln His Pro Trp Leu Gln Pro
             290                 295

<210> SEQ ID NO 2
<211> LENGTH: 287
<212> TYPE: PRT
<213> ORGANISM: Homo sapiens
<220> FEATURE: -
<223> OTHER INFORMATION: 132750

<400> SEQUENCE: 2

Met Gln Glu Ile Pro Gln Glu Gln Ile Lys Glu Ile Lys Lys Glu
  1               5                  10                  15

Gln Leu Ser Gly Ser Pro Trp Ile Leu Arg Glu Asn Glu Val
             20                  25                  30

Ser Thr Leu Tyr Lys Gly Glu Tyr His Arg Ala Pro Val Ala Ile
             35                  40                  45

Lys Val Phe Lys Lys Leu Gln Ala Gly Ser Ile Ala Ile Val Arg
             50                  55                  60

Gln Thr Phe Asn Lys Glu Ile Lys Thr Met Lys Lys Phe Glu Ser
             65                  70                  75

Pro Asn Ile Leu Arg Ile Phe Gly Ile Cys Ile Asp Glu Thr Val
             80                  85                  90

Thr Pro Pro Gln Phe Ser Ile Val Met Glu Tyr Cys Glu Leu Gly
             95                 100                 105

Thr Leu Arg Glu Leu Leu Asp Arg Glu Lys Asp Leu Thr Leu Gly
             110                 115                 120

Lys Arg Met Val Leu Val Leu Gly Ala Ala Arg Gly Leu Tyr Arg
             125                 130                 135
```

```
Leu His His Ser Glu Ala Pro Glu Leu His Gly Lys Ile Arg Ser
            140                 145                 150

Ser Asn Phe Leu Val Thr Gln Gly Tyr Gln Val Lys Leu Ala Gly
            155                 160                 165

Phe Glu Leu Arg Lys Thr Gln Thr Ser Met Ser Leu Gly Thr Thr
            170                 175                 180

Arg Glu Lys Thr Asp Arg Val Lys Ser Thr Ala Tyr Leu Ser Pro
            185                 190                 195

Gln Glu Leu Glu Asp Val Phe Tyr Gln Tyr Asp Val Lys Ser Glu
            200                 205                 210

Ile Tyr Ser Phe Gly Ile Val Leu Trp Glu Ile Ala Thr Gly Asp
            215                 220                 225

Ile Pro Phe Gln Gly Cys Asn Ser Glu Lys Ile Arg Lys Leu Val
            230                 235                 240

Ala Val Lys Arg Gln Gln Glu Pro Leu Gly Glu Asp Cys Pro Ser
            245                 250                 255

Glu Leu Arg Glu Ile Ile Asp Glu Cys Arg Ala His Asp Pro Ser
            260                 265                 270

Val Arg Pro Ser Val Asp Glu Ile Leu Lys Lys Leu Ser Thr Phe
            275                 280                 285

Ser Lys

<210> SEQ ID NO 3
<211> LENGTH: 346
<212> TYPE: PRT
<213> ORGANISM: Homo sapiens
<220> FEATURE: -
<223> OTHER INFORMATION: 507669

<400> SEQUENCE: 3

Met Gly Cys Gly Cys Ser Ser His Pro Glu Asp Asp Trp Met Glu
  1               5                  10                  15

Asn Ile Asp Val Cys Glu Asn Cys His Tyr Pro Ile Val Pro Leu
             20                  25                  30

Asp Gly Lys Gly Thr Leu Leu Ile Arg Asn Gly Ser Glu Val Arg
             35                  40                  45

Asp Pro Leu Val Thr Tyr Glu Gly Ser Asn Pro Pro Ala Ser Pro
             50                  55                  60

Leu Gln Asp Asn Leu Val Ile Ala Leu His Ser Tyr Glu Pro Ser
             65                  70                  75

His Asp Gly Asp Leu Gly Phe Glu Lys Gly Glu Gln Leu Arg Ile
             80                  85                  90

Leu Glu Gln Ser Gly Glu Trp Trp Lys Ala Gln Ser Leu Thr Thr
             95                 100                 105

Gly Gln Glu Gly Phe Ile Pro Phe Asn Phe Val Ala Lys Ala Asn
            110                 115                 120

Ser Leu Glu Pro Glu Ala Asn Leu Met Lys Gln Leu Gln His Gln
            125                 130                 135

Arg Leu Val Arg Leu Tyr Ala Val Val Thr Gln Glu Pro Ile Tyr
            140                 145                 150

Ile Ile Thr Glu Tyr Met Glu Asn Gly Ser Leu Val Asp Phe Leu
            155                 160                 165

Lys Thr Pro Ser Gly Ile Lys Leu Thr Ile Asn Lys Leu Leu Asp
            170                 175                 180

Met Ala Ala Gln Ile Ala Glu Gly Met Ala Phe Ile Glu Glu Arg
```

-continued

```
                185                 190                 195
Asn Tyr Ile His Arg Asp Leu Arg Ala Ala Asn Ile Leu Val Ser
                200                 205                 210
Asp Thr Leu Ser Cys Lys Ile Ala Asp Phe Gly Leu Ala Arg Leu
                215                 220                 225
Ile Glu Asp Asn Glu Tyr Thr Ala Arg Glu Gly Ala Lys Phe Pro
                230                 235                 240
Ile Lys Trp Thr Ala Pro Glu Ala Ile Asn Tyr Gly Thr Phe Thr
                245                 250                 255
Ile Lys Ser Asp Val Trp Ser Phe Gly Ile Leu Leu Thr Glu Ile
                260                 265                 270
Val Thr His Gly Arg Ile Pro Tyr Pro Gly Met Thr Asn Pro Glu
                275                 280                 285
Val Ile Gln Asn Leu Glu Arg Gly Tyr Arg Met Val Arg Pro Asp
                290                 295                 300
Asn Cys Pro Glu Glu Leu Tyr Gln Leu Met Arg Leu Cys Trp Lys
                305                 310                 315
Glu Arg Pro Glu Asp Arg Pro Thr Phe Asp Tyr Leu Arg Ser Val
                320                 325                 330
Leu Glu Asp Phe Phe Thr Ala Thr Glu Gly Gln Tyr Gln Pro Gln
                335                 340                 345
Pro

<210> SEQ ID NO 4
<211> LENGTH: 90
<212> TYPE: PRT
<213> ORGANISM: Homo sapiens
<220> FEATURE: -
<223> OTHER INFORMATION: 1439938

<400> SEQUENCE: 4

Met Pro Ala Gly Gly Arg Ala Gly Ser Leu Lys Asp Pro Asp Val
  1               5                  10                  15
Ala Glu Leu Phe Phe Lys Asp Pro Glu Lys Leu Phe Ser Asp
                 20                  25                  30
Leu Arg Glu Ile Gly His Gly Ser Phe Gly Ala Val Tyr Phe Ala
                 35                  40                  45
Arg Asp Val Arg Asn Ser Glu Val Val Ala Ile Lys Lys Met Ser
                 50                  55                  60
Tyr Ser Gly Lys Gln Ser Asn Glu Lys Trp Gln Asp Ile Ile Lys
                 65                  70                  75
Glu Val Arg Arg Arg Arg Val Gly Arg Glu Asp Glu Arg
                 80                  85                  90

<210> SEQ ID NO 5
<211> LENGTH: 327
<212> TYPE: PRT
<213> ORGANISM: Homo sapiens
<220> FEATURE: -
<223> OTHER INFORMATION: 1447427

<400> SEQUENCE: 5

Met Ser Ser Phe Leu Pro Glu Gly Gly Cys Tyr Glu Leu Leu Thr
  1               5                  10                  15
Val Ile Gly Lys Gly Phe Glu Asp Leu Met Thr Val Asn Leu Ala
                 20                  25                  30
Arg Tyr Lys Pro Thr Gly Glu Tyr Val Thr Val Arg Arg Ile Asn
```

-continued

```
                35                  40                  45
Leu Glu Ala Cys Ser Asn Glu Met Val Thr Phe Leu Gln Gly Glu
                50                  55                  60

Leu His Val Ser Lys Leu Phe Asn His Pro Asn Ile Val Pro Tyr
                65                  70                  75

Arg Ala Thr Phe Ile Ala Asp Asn Glu Leu Trp Val Val Thr Ser
                80                  85                  90

Phe Met Ala Tyr Gly Ser Ala Lys Asp Leu Ile Cys Thr His Phe
                95                 100                 105

Met Asp Gly Met Asn Glu Leu Ala Ile Ala Tyr Ile Leu Gln Gly
               110                 115                 120

Val Leu Lys Ala Leu Asp Tyr Ile His His Met Gly Tyr Val His
               125                 130                 135

Arg Ser Val Lys Ala Ser His Ile Leu Ile Ser Val Asp Gly Lys
               140                 145                 150

Val Tyr Leu Ser Gly Leu Arg Thr Thr Leu Ser Met Ile Ser His
               155                 160                 165

Gly Gln Arg Gln Arg Val Val His Asp Phe Pro Lys Tyr Ser Val
               170                 175                 180

Lys Val Leu Pro Trp Leu Ser Pro Glu Val Leu Gln Gln Asn Leu
               185                 190                 195

Gln Gly Tyr Asp Ala Lys Ser Asp Ile Tyr Ser Val Gly Ile Thr
               200                 205                 210

Ala Cys Glu Leu Ala Asn Gly His Val Pro Phe Lys Asp Met Pro
               215                 220                 225

Ala Thr Gln Met Leu Leu Glu Lys Leu Asn Gly Thr Val Pro Cys
               230                 235                 240

Leu Leu Asp Thr Ser Thr Ile Pro Ala Glu Glu Leu Thr Met Ser
               245                 250                 255

Pro Ser Arg Ser Val Ala Asn Ser Gly Leu Ser Asp Ser Leu Thr
               260                 265                 270

Thr Ser Thr Pro Arg Pro Ser Asn Gly Asp Ser Pro Ser His Pro
               275                 280                 285

Tyr His Arg Thr Phe Ser Pro His Phe His His Phe Val Glu Gln
               290                 295                 300

Cys Leu Gln Arg Asn Pro Asp Ala Arg Tyr Pro Cys Trp Pro Gly
               305                 310                 315

Pro Gly Leu Arg Glu Ser Arg Gly Cys Ser Gly Gly
               320                 325
```

<210> SEQ ID NO 6
<211> LENGTH: 345
<212> TYPE: PRT
<213> ORGANISM: Homo sapiens
<220> FEATURE: -
<223> OTHER INFORMATION: 1567782

<400> SEQUENCE: 6

```
Met Glu Lys Tyr Val Arg Leu Gln Lys Ile Gly Glu Gly Ser Phe
  1                   5                  10                  15

Gly Lys Ala Ile Leu Val Lys Ser Thr Glu Asp Gly Arg Gln Tyr
                 20                  25                  30

Val Ile Lys Glu Ile Asn Ile Ser Arg Met Ser Ser Lys Glu Arg
                 35                  40                  45

Glu Glu Ser Arg Arg Glu Val Ala Val Leu Ala Asn Met Lys His
```

-continued

```
                50                  55                  60
Pro Asn Ile Val Gln Tyr Arg Glu Ser Phe Glu Gly Ile Leu Asp
                65                  70                  75
Trp Phe Val Gln Ile Cys Leu Ala Leu Lys His Val His Asp Arg
                80                  85                  90
Lys Ile Leu His Arg Asp Ile Lys Ser Gln Asn Ile Phe Leu Thr
                95                 100                 105
Lys Asp Gly Thr Val Gln Leu Gly Asp Phe Gly Ile Ala Arg Val
               110                 115                 120
Leu Asn Ser Thr Val Glu Leu Ala Arg Thr Cys Ile Gly Thr Pro
               125                 130                 135
Tyr Tyr Leu Ser Pro Glu Ile Cys Glu Asn Lys Pro Tyr Asn Asn
               140                 145                 150
Lys Ser Asp Ile Trp Ala Leu Gly Cys Val Leu Tyr Glu Leu Cys
               155                 160                 165
Thr Leu Lys His Ala Phe Glu Ala Gly Ser Met Lys Asn Leu Val
               170                 175                 180
Leu Lys Ile Ile Ser Gly Ser Phe Pro Pro Val Ser Leu His Tyr
               185                 190                 195
Ser Tyr Asp Leu Arg Ser Leu Val Ser Gln Leu Phe Lys Arg Asn
               200                 205                 210
Pro Arg Asp Arg Pro Ser Val Asn Ser Ile Leu Glu Lys Gly Phe
               215                 220                 225
Ile Ala Lys Arg Ile Glu Lys Phe Leu Ser Pro Gln Leu Ile Ala
               230                 235                 240
Glu Glu Phe Cys Leu Lys Thr Phe Ser Lys Phe Gly Ser Gln Pro
               245                 250                 255
Ile Pro Ala Lys Arg Pro Ala Ser Gly Gln Asn Ser Ile Ser Val
               260                 265                 270
Met Pro Ala Gln Lys Ile Thr Lys Pro Ala Ala Lys Tyr Gly Ile
               275                 280                 285
Pro Leu Ala Tyr Lys Lys Tyr Gly Asp Lys Lys Leu His Glu Lys
               290                 295                 300
Lys Pro Leu Gln Lys His Lys Gln Ala His Gln Thr Pro Glu Lys
               305                 310                 315
Arg Val Asn Thr Gly Glu Glu Arg Arg Lys Ile Ser Glu Glu Ala
               320                 325                 330
Ala Arg Lys Arg Arg Leu Glu Phe Ile Glu Lys Asp Lys Glu Arg
               335                 340                 345
```

<210> SEQ ID NO 7
<211> LENGTH: 424
<212> TYPE: PRT
<213> ORGANISM: Homo sapiens
<220> FEATURE: -
<223> OTHER INFORMATION: 2295842

<400> SEQUENCE: 7

```
Met Ile Ser Phe Cys Pro Asp Cys Gly Lys Ser Ile Gln Ala Ala
  1               5                  10                  15
Phe Lys Phe Cys Pro Tyr Cys Gly Asn Ser Leu Pro Val Glu Glu
                 20                  25                  30
His Val Gly Ser Gln Thr Phe Val Asn Pro His Val Ser Ser Phe
                 35                  40                  45
Gln Gly Ser Gly Ser Arg Pro Pro Thr Pro Lys Ser Ser Pro Gln
```

```
                    50                  55                  60
Lys Thr Arg Lys Ser Pro Gln Val Thr Arg Gly Ser Pro Gln Lys
                65                  70                  75
Thr Ser Cys Ser Pro Gln Lys Thr Arg Gln Ser Pro Gln Thr Leu
                80                  85                  90
Lys Arg Ser Arg Val Thr Thr Ser Leu Glu Ala Leu Pro Thr Gly
                95                 100                 105
Thr Val Leu Thr Asp Lys Ser Gly Arg Gln Trp Lys Leu Lys Ser
               110                 115                 120
Phe Gln Thr Arg Asp Asn Gln Gly Ile Leu Tyr Glu Ala Ala Pro
               125                 130                 135
Thr Ser Thr Leu Thr Cys Asp Ser Gly Pro Gln Lys Gln Lys Phe
               140                 145                 150
Ser Leu Lys Leu Asp Ala Lys Asp Gly Arg Leu Phe Asn Glu Gln
               155                 160                 165
Asn Phe Phe Gln Arg Ala Ala Lys Pro Leu Gln Val Asn Lys Trp
               170                 175                 180
Lys Lys Leu Tyr Ser Thr Pro Leu Leu Ala Ile Pro Thr Cys Met
               185                 190                 195
Gly Phe Gly Val His Gln Asp Lys Tyr Arg Phe Leu Val Leu Pro
               200                 205                 210
Ser Leu Gly Arg Ser Leu Gln Ser Ala Leu Asp Val Ser Pro Lys
               215                 220                 225
His Val Leu Ser Glu Arg Ser Val Leu Gln Val Ala Cys Arg Leu
               230                 235                 240
Leu Asp Ala Leu Glu Phe Leu His Glu Asn Glu Tyr Val His Gly
               245                 250                 255
Asn Val Thr Ala Glu Asn Ile Phe Val Asp Pro Glu Asp Gln Ser
               260                 265                 270
Gln Val Thr Leu Ala Gly Tyr Gly Phe Ala Phe Arg Tyr Cys Pro
               275                 280                 285
Ser Gly Lys His Val Ala Tyr Val Glu Gly Ser Arg Ser Pro His
               290                 295                 300
Glu Gly Asp Leu Glu Phe Ile Ser Met Asp Leu His Lys Gly Cys
               305                 310                 315
Gly Pro Ser Arg Arg Ser Asp Leu Gln Ser Leu Gly Tyr Cys Met
               320                 325                 330
Leu Lys Trp Leu Tyr Gly Phe Leu Pro Trp Thr Asn Cys Leu Pro
               335                 340                 345
Asn Thr Glu Asp Ile Met Lys Gln Lys Gln Lys Phe Val Asp Lys
               350                 355                 360
Pro Gly Pro Phe Val Gly Pro Cys Gly His Trp Ile Arg Pro Ser
               365                 370                 375
Glu Thr Leu Gln Lys Tyr Leu Lys Val Val Met Ala Leu Thr Tyr
               380                 385                 390
Glu Glu Lys Pro Pro Tyr Ala Met Leu Arg Asn Asn Leu Glu Ala
               395                 400                 405
Leu Leu Gln Asp Leu Arg Val Ser Pro Tyr Asp Pro Ile Gly Leu
               410                 415                 420
Pro Met Val Pro

<210> SEQ ID NO 8
<211> LENGTH: 99
```

```
<212> TYPE: PRT
<213> ORGANISM: Homo sapiens
<220> FEATURE: -
<223> OTHER INFORMATION: 2605059

<400> SEQUENCE: 8

Met Pro Leu Glu Glu Val Leu Pro Asp Val Ser Pro Gln Ala Leu
 1               5                  10                  15

Asp Leu Leu Gly Gln Phe Leu Leu Tyr Pro Pro His Gln Arg Ile
                20                  25                  30

Ala Ala Ser Lys Ala Leu Leu His Gln Tyr Phe Phe Thr Ala Pro
            35                  40                  45

Leu Pro Ala His Pro Ser Glu Leu Pro Ile Pro Gln Arg Leu Gly
        50                  55                  60

Gly Pro Ala Pro Lys Ala His Pro Gly Pro His Ile His Asp
65                  70                  75

Phe His Val Asp Arg Pro Leu Glu Glu Ser Leu Leu Asn Ser Glu
                80                  85                  90

Leu Ile Arg Pro Phe Ile Leu Glu Gly
                95

<210> SEQ ID NO 9
<211> LENGTH: 138
<212> TYPE: PRT
<213> ORGANISM: Homo sapiens
<220> FEATURE: -
<223> OTHER INFORMATION: 3000825

<400> SEQUENCE: 9

Met Trp Val Val Pro Pro Ile Gly Ala Glu Phe Leu Gly Thr Glu
 1               5                  10                  15

Lys Gly Gly Leu Arg Asp Gln Lys Thr Pro Asp Asp His Glu Ala
                20                  25                  30

Glu Thr Gly Ile Lys Ser Lys Glu Ala Arg Lys Tyr Ile Phe Asn
            35                  40                  45

Cys Leu Asp Ala Cys Val Gln Val Asn Met Thr Thr Asp Leu Glu
        50                  55                  60

Gly Ser Asp Met Leu Val Glu Lys Ala Asp Arg Arg Glu Phe Ile
65                  70                  75

Asp Leu Leu Lys Lys Met Leu Thr Ile Asp Ala Asp Lys Arg Ile
                80                  85                  90

Thr Pro Ile Glu Thr Leu Asn His Pro Phe Val Thr Met Thr His
                95                 100                 105

Leu Leu Asp Phe Pro His Ser Thr His Val Lys Ser Cys Phe Gln
                110                 115                 120

Asn Met Glu Ile Cys Lys Arg Arg Val Asn Met Tyr Asp Thr Val
                125                 130                 135

Asn Gln Ser

<210> SEQ ID NO 10
<211> LENGTH: 1427
<212> TYPE: DNA
<213> ORGANISM: Homo sapiens
<220> FEATURE: -
<223> OTHER INFORMATION: 119819

<400> SEQUENCE: 10
cggagccaca gtggctccac cccccacctt cacgcactcc cacggtggta atcccgaaag    60
```

```
gctgggtggc tgggctgacg gtaattcccg ggggggtca agtgcccaa actgctcttg      120 gtgaaaggat gctgtcttcc ccgaatggcc acttccgcct gccttagctt gggctgagag    180
gggacagaga gcaccctgag gcgggccggc caggtcttcc cactcctaat ggagctgtgg    240
ggagtggggc cacaggcggg gaggcaggga gagtagtgag tagctggtgc caaggggcgc    300
tggcgccaca ttctggtgtc catgggagcc ctggggcccg gagaggcctc ttccctggcg    360
gctgtgcagg gaaacctcca cttcatgctg actggggcgg gcgacaggaa ccctggggtg    420
accctggctc tgacagcaga ccggtaagct gtccaaaaac aagaggaaga agatgaggcg    480
caaacggaaa cagcagaagc ggctgctgga ggagcggctg cgggacctgc agaggctgga    540
ggccatggag gctgccaccc aggctgagga ctctggcttg agactagacg ggggcagcgg    600
ctccacatcc tcttcaggct gtcaccccgg gggcgccaga gcaggtccct ccccagcctc    660
ttcctccccc gccccagggg gcggccgtag cctcagcgcg ggctcacaga cctcaggctt    720
ctccggctcc ctcttctctc ctgcctcctg ctccatcctc tccggctcgt ccaatcagcg    780
agagaccggg ggcctcctgt cgcctagcac accattcggt gcctcgaacc tcctggtgaa    840 cccctggag ccccaaaatg cagataagat caagatcaag atcgcagacc tgggcaacgc    900
ctgctgggtg cacaagcact tcacggaaga catccagact cggcagtacc gggccgtcga    960
ggtgctgatc ggcgccgaat acggcccccc ggcagacatc tggagcacag cctgcatggc   1020
cttcgagctg gccactggtg actacctgtt cgagccgcat tctggagaag actacagtcg   1080
tgatgaggac cacatcgctc acatagtgga gcttctgggg gacatccccc agccttcgc    1140 cctctcaggc cgctattccc gggagttctt caaccggaga ggagagctgc ggcacatcca   1200
caatctcaag cactggggcc tgtacgaggt actcatgaa aagtacgagt ggcccctaga    1260
gcaggccaca cagttcagcg cctttctgct gcccatgaat gagtacatcc ccgaaaagcg   1320
ggccagtgcc cgtgactgcc tccagcaccc ctggctccaa ccctagggcc cggctgtggc   1380
tccacctcca gctctccgtg cctttaaggg aaaagcggga cagctcc                 1427
```

<210> SEQ ID NO 11
<211> LENGTH: 1586
<212> TYPE: DNA
<213> ORGANISM: Homo sapiens
<220> FEATURE: -
<223> OTHER INFORMATION: 132750

<400> SEQUENCE: 11

```
gctcattgac tcttttgtct tctttcctct cgggggtgag gtcagattta ccaccaaaat     60
gcatgcagga gatcccgcaa gagcaaatca aggagatcaa gaaggagcag ctttcaggat    120
ccccgtggat tctgctaagg gaaaatgaag tcagcacact ttataaagga gaataccaca    180
gagctccagt ggccataaaa gtattcaaaa aactccaggc tggcagcatt gcaatagtga    240
ggcagacttt caataaggag atcaaaacca tgaagaaatt cgaatctccc aacatcctgc    300
gtatatttgg gatttgcatt gatgaaacag tgactccgcc tcaattctcc attgtcatgg    360
agtactgtga actcgggacc ctgagggagc tgttggatag ggaaaaagac ctcacacttg    420
gcaagcgcat ggtcctagtc ctgggggcag cccgaggcct ataccggcta caccattcag    480
aagcacctga actccacgga aaaatcagaa gctcaaactt cctggtaact caaggctacc    540
aagtgaagct tgcaggattt gagttgagga aaacacagac ttccatgagt ttgggaacta    600
cgagagaaaa gacagacaga gtcaaatcta cagcatatct ctcacctcag gaactggaag    660
atgtatttta tcaatatgat gtaaagtctg aaatatacag ctttggaatc gtcctctggg    720
```

```
aaatcgccac tggagatatc ccgtttcaag gctgtaattc tgagaagatc cgcaagctgg      780
tggctgtgaa gcggcagcag gagccactgg gtgaagactg cccttcagag ctgcgggaga      840
tcattgatga gtgccgggcc catgatccct ctgtgcggcc ctctgtggat gaaatcttaa      900
agaaactctc cacctttcct aagtagtgta tcaaaatcta aaccaaggag tctctggaca      960
agaagctggg agaggcacaa actggacatc tctctctctc atatccttcg gcattgggtt     1020
atctatggga gcaaggagtg ggcacgcttc tctgttacaa atagaaaacg attccagtca     1080
tacaggacac atcccactcc aaatgatatt tccaaaaaca tacctctgac agtaactttg     1140
atagatggtt tgtcaaatgt atctttctgg gtatccacac ctcttggcaa tgaaatttgc     1200
agctcctccc ttccataaat gaagtctctt tccccaccat ttgaatctgg gctggcactg     1260
tgacttgatt tgatcaatag aatgtggaag aagtgactgt atgccagttc aagcctagg      1320 tttcaagagg cctataaat gtctgttgga accttaccca gccatgaaca tgttgagtga      1380
gcatgctgga gaatgagaga ccacatgaag cagaaacatg ctttcctagc tgaagtcata     1440
ctagcccaac caacatggca gctaacacat gaatgaggcc aatcaagacc agaagaacca     1500
ctcaagcaga tcccagccca aattgcccat tcacacaatc aggagctaaa taaattactg     1560
ttgtcttaac actaaaaaaa aaaaaa                                          1586

<210> SEQ ID NO 12
<211> LENGTH: 1574
<212> TYPE: DNA
<213> ORGANISM: Homo sapiens
<220> FEATURE: -
<223> OTHER INFORMATION: 507669

<400> SEQUENCE: 12
cgacggcgaa gggagctgag actgtccagg cagccaggtt aggccaggag gaccatgtga       60
atggggccag aaggctcccg ggctgggcag ggaccatggg ctgtggctgc agctcacacc      120
cggaagatga ctggatggaa acatcgatg tgtgtgagaa ctgccattat cccatagtcc       180
cactggatgg caagggcacg ctgctcatcc gaaatggctc tgaggtgcgg gacccactgg      240
ttacctacga aggctccaat ccgccggctt ccccactgca agacaacctg gttatcgctc      300
tgcacagcta tgagccctct cacgacggag atctgggctt tgagaagggg gaacagctcc      360
gcatcctgga gcagagcggc gagtggtgga aggcgcagtc cctgaccacg ggccaggaag      420
gcttcatccc cttcaatttt gtggccaaag cgaacagcct ggagcccgag gccaacctca      480
tgaagcagct gcaacaccag cggctggttc ggctctacgc tgtggtcacc caggagccca      540
tctacatcat cactgaatac atgagaaatg ggagtctagt ggattttctc aagacccctt      600
caggcatcaa gttgaccatc aacaaactcc tggacatggc agcccaaatt gcagaaggca      660
tggcattcat tgaagagcgg aattatattc atcgtgacct tcgggctgcc aacattctgg      720
tgtctgacac cctgagctgc aagattgcag actttggcct agcacgcctc attgaggaca      780
acgagtacac agcccaggag gggccaagt tccccattaa gtggacagcg ccagaagcca      840
ttaactacgg gacattcacc atcaagtcag atgtgtggtc ttttgggatc ctgctgacgg      900
aaattgtcac ccacggccgc atcccttacc cagggatgac caacccggag gtgattcaga     960
acctggagcg aggctaccgc atggtgcgcc ctgacaactg tccagaggag ctgtaccaac     1020
tcatgaggct gtgctggaag gagcgcccag aggaccggcc caccttgac tacctgcgca     1080 gtgtgctgga ggacttcttc acggccacag agggccagta ccagcctcag ccttgagagg     1140
```

-continued

| | | | |
|---|---|---|---|
| ccttgagagg ccctgggtt ctcccctttt ctctccagcc tgacttgggg agatggagtt | | | 1200 |
| cttgtgccat agtcacatgg cctatgcaca tatggactct gcacatgaat cccacccaca | | | 1260 |
| tgtgacacat atgcaccttg tgtctgtaca cgtgtcctgt agttgcgtgg actctgcaca | | | 1320 |
| tgtcttgtac atgtgtagcc tgtgcatgta tgtcttggac actgtacaag gtaccccttt | | | 1380 |
| ctggctctcc catttcctga gaccacagag agagggaga agcctgggat tgacagaagc | | | 1440 |
| ttctgcccac ctactttct ttcctcagat catccagaag ttcctcaagg gccaggactt | | | 1500 |
| tatctaaatac ctctgtgtgc tcctccttgg tgcctggcct ggcacacatc aggagttcaa | | | 1560 |
| taaatgtctg ttga | | | 1574 |

<210> SEQ ID NO 13
<211> LENGTH: 1866
<212> TYPE: DNA
<213> ORGANISM: Homo sapiens
<220> FEATURE: -
<223> OTHER INFORMATION: 1439938

<400> SEQUENCE: 13

| | | | |
|---|---|---|---|
| cgggaggaag agggagaggg agaccgggac gagaccgggg ctgtggtgcg gagagaggct | | | 60 |
| gagacggaga agaggagagg cagagagggc gcggggaccg tcagcagcac cttagctaca | | | 120 |
| atcgttcagc tattctcgga agagagaagg gagagggagg aggccgggc gggagtgggg | | | 180 |
| gctgtcaccc tcggacccg gcgtgagagg ggccgtgcgg ccggacgtcc tcggggtggg | | | 240 |
| cccccagtcg gtggccgaag acctacagct caggcccctg ggtcccaaat ttccaggctt | | | 300 |
| tgcccctcct cctttctcag atacccgggt aacagtcctc atagtccaga tatccgggac | | | 360 |
| tcgggtccca acctctctaa acctgggtct ctgtttcata gaatttcaaa tatcaggttc | | | 420 |
| aggcccctgc gtgcaccagt atccggggtt cattccccgg gcgttcagat atcggattca | | | 480 |
| gtctccatcc cgttcagata ttcggggttc agacccccaca atcagaaatc cggaattcgg | | | 540 |
| cagctgtcgc cctcgacgag ggggaggact ggaccgcgag gtcagattag gttgtcaccc | | | 600 |
| cctcccctcc aggggaggct tcccgggccc gccctcagg aagggcgaaa gccgaggaag | | | 660 |
| aggtggcaag gggaaaggtc tccttgcccc tctccctgct tggcagagcc gctggaggac | | | 720 |
| cccaggcgga agcggaggcg ctggggcacc atagtgaccc ctaccaggcc aggccccact | | | 780 |
| ctcagggccc ccaggggcca ccatgccagc tgggggccgg gccgggagcc tgaaggaccc | | | 840 |
| agatgtggct gagctcttct tcaaggatga cccagaaaag ctcttctctg acctccggga | | | 900 |
| aattggccat ggcagctttg gagccgtata cttttgcccgg gatgtccgga atagtgaggt | | | 960 |
| ggtggccatc aagaagatgt cctacagtgg gaagcagtcc aatgagaaat ggcaagacat | | | 1020 |
| catcaaggag gtgcggagac aaggagagt agggagggag gatgaagaga gataaggggg | | | 1080 |
| agaaaagaga ggggcatgag agtggagcgg agctaagaag gggtagaaga gagagtgggt | | | 1140 |
| gaagggaag agacgtagag aaagtgtgga gagaggaaag gcatagcgag agaacgaggg | | | 1200 |
| agagagaagt ggaaggggga agtaagagag gataagagga acgagaggag gggaagggtg | | | 1260 |
| gggacgagaa cgaagagcat gatggagagg aaagatagag aagagaggaa gtggaggcag | | | 1320 |
| ttagggggca tggaggagag agagagatga gggagagtgg gagcacgggg cggatggacg | | | 1380 |
| gggtggagaa gaagagaggg aggagatgag aggaggaaga ggtgggagaa ccgagcgagg | | | 1440 |
| gaaaagatgg aggaggcagt agagagggtg tgcaagggggt gaaaagaaag aagaaggaaa | | | 1500 |
| aggatggagg gagtgaaggt aggagacgag gaggagggat gggagagaat ggagggtagc | | | 1560 |
| gtgtggatgg tgagtggtag agaatagtga gatggtgaga agcggagaaa ggcagcagag | | | 1620 |

```
gatggggtg aagcgggaag caaagacaat aggggatgga ggaggagagg agcaggagga    1680
agacgaagag cgaagggctt gaaagaggga gaagagagta gtaagggta ggtatgtaga    1740 tgcgagtagg agaggaagag aaggaatgaa tgagagagag tagagagtag agagagaacg   1800
aaggaacggg gcagagggag aggaaggaca gaaggagaag agaacaatcg aagaatgaga   1860
gtgttt                                                              1866
```

<210> SEQ ID NO 14
<211> LENGTH: 1498
<212> TYPE: DNA
<213> ORGANISM: Homo sapiens
<220> FEATURE:
<221> NAME/KEY: unsure
<222> LOCATION: 1350, 1355, 1372, 1444
<223> OTHER INFORMATION: a or g or c or t, unknown, or other
<220> FEATURE: -
<223> OTHER INFORMATION: 1447427

<400> SEQUENCE: 14

```
ctcccctccc agcaaccggt ctggcggcgg cgcggcagta aaactgagga ggcggagcaa     60
gacggtcggg gctgcttgct aactccagga acaggtttaa gttttgaaa ctgaagtagg    120 tctacacagt aggaactcat gtcatttctt gtaagtaaac ccagagcgaa tccaggacca   180
atgatgcgag ctcagagtca atagcatcct tctctaaaca ggaggtcatg agtagctttc   240
tgccagaggg agggtgttac gagctgctca ctgtgatagg caaaggattt gaggacctga   300
tgactgtgaa tctagcaagg tacaaaccaa caggagagta cgtgactgta cggaggatta   360
acctagaagc ttgttccaat gagatggtaa cattcttgca gggcgagctg catgtctcca   420
aactcttcaa ccatcccaat atcgtgccat atcgagccac ttttattgca gacaatgagc   480
tgtgggttgt cacatcattc atggcatacg gttctgcaaa agatctcatc tgtacacact   540
tcatggatgg catgaatgag ctggcgattg cttacatcct gcaggggtg ctgaaggccc   600 tcgactacat ccaccacatg ggatatgtac acaggagtgt caaagccagc cacatcctga   660
tctctgtgga tgggaaggtc tacctgtctg gtttgcgcac aacgctcagc atgataagcc   720
atgggcagcg gcagcgagtg gtccacgatt ttcccaagta cagtgtcaag gttctgccgt   780
ggctcagccc cgaggtcctc cagcagaatc tccagggtta tgatgccaag tctgacatct   840
acagtgtggg aatcacagcc tgtgaactgg ccaacggcca tgtcccctt aaggatatgc   900 ctgccaccca gatgctgcta gagaaactga acggcacagt gccctgcctg ttggatacca   960
gcaccatccc cgctgaggag ctgaccatga gcccttcgcg ctcagtggcc aactctggcc   1020
tgagtgacag cctgaccacc agcacccccc ggccctccaa cggtgactcg ccctcccacc   1080
cctaccaccg aaccttctcc ccccacttcc accactttgt ggagcagtgc cttcagcgca   1140
acccggatgc caggtatccc tgctggcctg ggcctgggct tcgggagagc agagggtgct   1200
caggagggta aggccagggt gtgaagggac ttacctccca aaggttctgc agggaatct    1260 ggagctacac acaggaggga tcagctcctg ggtgtgtcag aggccagcct ggggagctct   1320
ggccactgct tcccatgagc tgagggagan ggagnaggga cccgaggctg angcataagt   1380
ggcaggattt tcggaagctg gggacacggc agtgatgctg cggtctctcc ctcccttacc   1440
tcangctcag tgcagcaccc tctgaacact ctttctcagc agtatcgtag ccttcgtt    1498
```

<210> SEQ ID NO 15
<211> LENGTH: 1846
<212> TYPE: DNA

<213> ORGANISM: Homo sapiens
<220> FEATURE: -
<223> OTHER INFORMATION: 1567782

<400> SEQUENCE: 15

```
taggaattcg tcgacccacg cgatccgccg tcagaagact gccacaccta gactgatgct    60
tattagtcat caccgttatt cctactaacg tcctgtgtca ctgagttttt taaatgtcta   120
gcatatctgt aaagatgcct tagaaaaaga atcatggaga agtatgttag actacagaag   180
attggagaag gttcatttgg aaaagccatt cttgttaaat ctacagaaga tggcagacag   240
tatgttatca aggaaattaa catctcaaga atgtccagta agaaagaga agaatcaagg    300
agagaagttg cagtattggc aaacatgaag catccaaata ttgtccagta tagagaatca   360
tttgaaggaa ttttggactg gtttgtacag atatgtttgg ccctgaaaca tgtacatgat   420
agaaaaattc ttcatcgaga cattaaatct cagaacatat ttttaactaa agatggaaca   480
gtacaacttg gagattttgg aattgctaga gttcttaata gtactgtaga gctggctcga   540
acttgcatag ggaccccata ctacttgtca cctgaaatct gtgaaaacaa accttacaat   600
aataaaagtg acatttgggc tctggggtgt gtcctttatg agctgtgtac acttaaacat   660
gcttttgaag ctggcagtat gaaaaacctg gtactgaaga taatatctgg atcttttcca   720
cctgtgtctt tgcattattc ctatgatctc cgcagtttgg tgtctcagtt atttaaaaga   780
aatcctaggg atagaccatc agtcaactcc atattggaga aggtttat agccaaacgc     840
attgaaaagt ttctctctcc tcagcttatt gcagaagaat tttgtctaaa acatttcg     900
aagtttggat cacagcctat accagctaaa agaccagctt caggacaaaa ctcgatttct   960
gttatgcctg ctcagaaaat tacaaagcct gccgctaaat atggaatacc tttagcatat  1020
aagaaatatg gagataaaaa attacacgaa aagaaaccac tgcaaaaaca taaacaggcc  1080
catcaaactc cagagaagag agtgaatact ggagaagaaa ggaggaaaat atctgaggaa  1140
gcagcaagaa agagaaggct ggaatttatt gaaaaagata aggaacggta ggatcagatt  1200
attagtttaa tgaaggctga acaaatgaaa aggcaagaca aggaaaggtt ggaaagaata  1260
aatagggcca gggaacaagg atggagaaat gtgctaagtg ctggtggaag tggtgaagta  1320
aaggtaggca ttttatacca atatggttat actaccattt tcccctccag ttccaccttg  1380
ttctataaaa tgcatgtact tgggatttc tttctttctt tagtgtacaa ttaattttta  1440
cctagaattc tttaacattt attatgaata cttagctttc ctgcatgtat ctgatatgta  1500
acttgtgttg ctgttatgtg actatactca aaattgcttt aaaagttttt tgtgaagact  1560
atgataacat tattcctgtc aggaattttt aaaaattatg tacaattcat gacactgcag  1620
cctaaaatcg ttctgtaatt tcatgtagcc ttgaagatta agttctcaga agatgcttct  1680
taaatccgat ccctgttgtc tctccaattt catcaccatt cattcccta ccacatactg    1740
ggaagggcct attccatggc ggaaatgaag ggccataatt tgtaggtttt ccattaccaa  1800
taatgggggg ttggcccaaa tcctactttt gggcctttgg aacctt                  1846
```

<210> SEQ ID NO 16
<211> LENGTH: 1721
<212> TYPE: DNA
<213> ORGANISM: Homo sapiens
<220> FEATURE: -
<223> OTHER INFORMATION: 2295842

<400> SEQUENCE: 16

```
agttggacga ggctcagtga aagttttcgc tgggcaactg agaaggtcgc tgtcaagatg    60
```

```
gagtttccaa cccagtaaat ccaagggcca gaccgtgacc tcataaagca tgatctcctt    120
ctgtccagac tgtggcaaaa gtatccaagc ggcattcaaa ttctgcccct actgtggaaa    180
ttctttgcct gtagaggagc atgtagggtc ccagaccttt gtcaatccac atgtgtcatc    240
cttccaaggc tccgggagca gaccccccaac ccccaaaagc agccctcaga agaccaggaa    300
gagccctcag gtgaccaggg gtagccctca gaagaccagc tgtagccctc agaagaccag    360
gcagagccct cagacgctga agcggagccg agtgaccacc tcacttgaag ctttgcccac    420
agggacagtg ctgacagaca agagtgggcg acagtggaag ctgaagtcct tccagaccag    480
ggacaaccag ggcattctct atgaagctgc acccacctcc accctcacct gtgactcagg    540
accacagaag caaaagttct cactcaaact ggatgccaag gatgggcgct tgttcaatga    600
gcagaacttc ttccagcggg ccgccaagcc tctgcaagtc aacaagtgga agaagctgta    660
ctcgacccca ctgctggcca tccctacctg catgggtttc ggtgttcacc aggacaaata    720
caggttcttg gtgttaccca gcctggggag gagccttcag tcggccctgg atgtcagccc    780
aaagcatgtg ctgtcagaga ggtctgtgct gcaggtggcc tgccggctgc tggatgccct    840
ggagttcctc catgagaatg agtatgttca tggaaatgtg acagctgaaa atatctttgt    900
ggatccagag gaccagagtc aggtgacttt ggcaggctat ggcttcgcct ccgctattg     960
cccaagtggc aaacacgtgg cctacgtgga aggcagcagg agccctcacg agggggacct   1020
tgagttcatt agcatggacc tgcacaaggg atgcgggccc tccgccgca gcgacctcca   1080
gagcctgggc tactgcatgc tgaagtggct ctacgggttt ctgccatgga caaattgcct   1140
tcccaacact gaggacatca tgaagcaaaa acagaagttt gttgataagc cggggcccctt   1200
cgtgggaccc tgcggtcact ggatcaggcc ctcagagacc ctgcagaagt acctgaaggt   1260
ggtgatggcc ctcacgtatg aggagaagcc gccctacgcc atgctgagga caacctaga   1320
agctttgctg caggatctgc gtgtgtctcc atatgacccc attggcctcc cgatggtgcc   1380
ctaggtggaa tccagaactt tccatttgca gtgtgcaaca gaaaaaaaaa aatgaagtaa   1440
tgtgactcaa ggcctgctgt ttaatcacag ataagcttct agaacaagcc ctggaatgtg   1500
cattcctgcc actggtttca ggatactcat cagtcctgat tagcctcccg gagggccccca   1560
gtttccctcc cgtgaatgtg aagttcccca tcttggtggc ctgcccttca gccagtgtcc   1620
tagcaaagct ggatggggtt gggccggcc acagggggga cccctcctac ccttgacacc   1680
tctgtgcttt ggtaataaat tgttttacca gaaaaaaaaa a                        1721
```

<210> SEQ ID NO 17
<211> LENGTH: 1985
<212> TYPE: DNA
<213> ORGANISM: Homo sapiens
<220> FEATURE: -
<223> OTHER INFORMATION: 2605059

<400> SEQUENCE: 17

```
ttcgcatctt gggcaccca aaccctcaag tctggccggt ttgtagggc ccttggtgag       60
gtgggtgtgg ggcaggttta ctccactccc aacagcaagt aaccactccc tcccctgaac   120
cttctctctc ctggccccaa cccccttga tggacaggga ccactgtcct ggcccaactc   180
agggcttcct ccttcctgct gtcatttggg ttggggtaga tcctgtcctt tgtccctttt   240
cacccctagta cacacatgtg cagtgtctca gcaagctgtg cacagagtcg tcatctgaga   300
gggcaagggg atggatgaag gaatacaggg gtgggtgagt gaatgaatga tgggtcaggg   360
```

-continued

```
agacacatgg atgggagagc acccccatg tgagtgtgtg ttagggctg agagttgaca      420 gcagagagca tggcaagggt cgggaactac tctcattgta ccctgttcct tctccctggc      480
ccaggagctc actgagctgc cggactacaa caagatctcc tttaaggagc aggtgcccat      540 gccctggag gaggtgctgc ctgacgtctc tccccaggca ttggatctgc tgggtcaatt      600
ccttctctac cctcctcacc agcgcatcgc agcttccaag gctctcctcc atcagtactt      660
cttcacagct ccctgcctg cccatccatc tgagctgccg attcctcagc gtctagggg      720 acctgccccc aaggccatc cagggccccc ccacatccat gacttccacg tggaccggcc      780
tcttgaggag tcgctgttga actcagagct gattcggccc ttcatcctgg aggggtgaga      840
agttggccct ggtcccgtct gcctgctcct caggaccact cagtccacct gttcctctgc      900
cacctgcctg gcttcaccct ccaaggcctc cccatggcca cagtgggccc acaccacacc      960 ctgccctta gccttgcga gggttggtct cgaggcagag gtcatgttcc cagccaagag     1020
tatgagaaca tccagtcgag cagaggagat tcatggcctg tgctcggtga gccttacctt     1080
ctgtgtgcta ctgacgtacc catcaggaca gtgagctctg ctgccagtca aggcctgcat     1140
atgcagaatg acgatgcctg ccttggtgct gcttccccga gtgctgcctc ctggtcaagg     1200
agaagtgcag agagtaaggt gtccttatgt tggaaactca agtggaagga agatttggtt     1260 tggtttatt ctcagagcca ttaaacacta gttcagtatg tgagatatag attctaaaaa     1320
cctcaggtgg ctctgcctta tgtctgttcc tccttcattt ctctcaaggg aaatggctaa     1380
ggtggcattg tctcatggct ctcgtttttg gggtcatggg gagggtagca ccaggcatag     1440 ccactttgc cctgagggac tcctgtgtgc ttcacatcac tgagcactca tttagaagtg     1500
agggagacag aagtctaggc ccaggatgg ctccagttgg ggatccagca ggagaccctc     1560
tgcacatgag gctggtttac caacatctac tccctcagga tgagcgtgag ccagaagcag     1620
ctgtgtattt aaggaaacaa gcgttcctgg aattaattta taaatttaat aaatcccaat     1680
ataatcccag ctagtgcttt ttccttatta taatttgata aggtgattat aaaagataca     1740
tggaaggaag tggaaccaga tgcagaagag gaaatgatgg aaggacttat ggtatcagat     1800
accaatattt aaaagtttgt ataataataa agagtatgat tgtggttcaa ggataaaaac     1860
agactagaga aacttattct tagccatcct ttatttttat tttatttatt ttttgatgga     1920
gtcttgctct gttgcccact gcaattcaag ccttggtgac agactctggt ctcaaaaaaa     1980
aaaaa                                                               1985
```

<210> SEQ ID NO 18
<211> LENGTH: 661
<212> TYPE: DNA
<213> ORGANISM: Homo sapiens
<220> FEATURE: -
<223> OTHER INFORMATION: 3000825

<400> SEQUENCE: 18

```
tgaggagtga tgaaagctgc atttcaactt aactgatgaa agcaggagca gtttacatcc       60
tgtcattcag atatatttgc aggtcccagc agcagccctc tccccttcct ggggcacagc      120
ccctctctgc ctttcctgca gagagaaaag ccacatcctg tgggcaatga caacatgtgg      180
gtggtgcctc ccataggggc agagttcctg ggaactgaga aggggggctt gagagatcag      240
aagacaccag atgaccatga agcagagaca gggattaagt caaaagaagc aagaaagtac      300
attttcaact gtttagatgc ttgcgtccag gtgaacatga cgacagattt ggaagggagc      360
gacatgttgg tagaaaaggc tgaccggcgg gagttcattg acctgttgaa gaagatgctg      420
```

-continued

```
accattgatg ctgacaagag aatcactcca atcgaaaccc tgaaccatcc ctttgtcacc    480
atgacacact tactcgattt tccccacagc acacacgtca aatcatgttt ccagaacatg    540
gagatctgca agcgtcgggt gaatatgtat gacacggtga accagagcta aacctagccc    600
caaacccctc tgccgaatat cctcgctcga gggccaaatt ccctatagtg gtcgtattac    660
g                                                                   661
```